(12) United States Patent
Al-Ali et al.

(10) Patent No.: US 8,529,301 B2
(45) Date of Patent: Sep. 10, 2013

(54) SHIELDED CONNECTOR ASSEMBLY

(75) Inventors: Ammar Al-Ali, Tustin, CA (US); Kevin Forrest, Rancho Santa Margarita, CA (US); Yassir Abdul-Hafiz, Irvine, CA (US); Eric Yang, Baldwin Park, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 13/399,762

(22) Filed: Feb. 17, 2012

(65) Prior Publication Data
US 2012/0276786 A1 Nov. 1, 2012

Related U.S. Application Data

(63) Continuation of application No. 12/248,856, filed on Oct. 9, 2008, now Pat. No. 8,118,620.

(60) Provisional application No. 60/979,674, filed on Oct. 12, 2007, provisional application No. 61/032,936, filed on Feb. 29, 2008.

(51) Int. Cl.
*H01R 9/22* (2006.01)

(52) U.S. Cl.
USPC .................. 439/709; 439/607.17; 439/607.5

(58) Field of Classification Search
USPC .......... 439/709, 909, 607.17, 607.05, 607.27, 439/607.3, 607.57, 607.58, 607.12, 607.15, 439/607.5, 607.51, 607.53, 607.55, 607.41
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,055,070 A | 10/1991 | Plegge et al. |
| 5,069,213 A | 12/1991 | Polczynski |
| 5,163,438 A | 11/1992 | Gordon et al. |
| 5,234,353 A | 8/1993 | Scholz et al. |
| 5,237,994 A | 8/1993 | Goldberger |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |

(Continued)

FOREIGN PATENT DOCUMENTS

| | | |
|---|---|---|
| JP | 6-505904 | 7/1994 |
| JP | 10-177881 | 6/1998 |
| WO | WO 92/16145 | 10/1992 |
| WO | WO97/48151 | 12/1997 |
| WO | WO 9748151 | 12/1997 |

OTHER PUBLICATIONS

Office Action for European Application No. 08 836 970.7 dated Mar. 19, 2012 in 11 pages.

(Continued)

*Primary Examiner* — Hae Moon Hyeon
(74) *Attorney, Agent, or Firm* — Knobbe Martens Olson & Bear, LLP

(57) ABSTRACT

A connector assembly according to embodiments of the present disclosure is advantageously configured to allow a sensor connector to straightforwardly and efficiently join with and detach from a patient cable connector. Further, embodiments of the connector assembly advantageously reduce un-shielded area in an electrical connection between a patient cable and a sensor connector. In addition, embodiments of the connector assembly advantageously increase the shielding of detector signals coming from the patient sensor to the monitor.

20 Claims, 42 Drawing Sheets

(56) References Cited

U.S. PATENT DOCUMENTS

| | | |
|---|---|---|
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,957,727 A | 9/1999 | Page, Jr. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| D422,560 S | 4/2000 | Lok |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,257,914 B1 | 7/2001 | Comerci et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| D509,803 S | 9/2005 | Titchener |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |

| | | |
|---|---|---|
| 6,970,792 B1 | 11/2005 | Diab |
| 6,979,812 B2 | 12/2005 | Al-Ali |
| D513,409 S | 1/2006 | Suckle |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| D519,465 S | 4/2006 | Sirichai et al. |
| 7,024,233 B2 | 4/2006 | Ali et al. |
| 7,027,849 B2 | 4/2006 | Al-Ali |
| 7,030,749 B2 | 4/2006 | Al-Ali |
| D520,459 S | 5/2006 | Kent et al. |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D524,759 S | 7/2006 | Wada et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| D567,183 S | 4/2008 | Victor |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,540,773 B2 | 6/2009 | Ko |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,753,709 B2 * | 7/2010 | Silkey et al. .................. 439/350 |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 * | 2/2012 | Al-Ali et al. .................. 439/709 |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |

| | | |
|---|---|---|
| 8,190,227 B2 | 5/2012 | Diab et al. |
| 8,203,438 B2 | 6/2012 | Kiani et al. |
| 8,224,411 B2 | 7/2012 | Al-Ali et al. |
| 2004/0147821 A1 | 7/2004 | Al-Ali et al. |
| 2006/0246780 A1 | 11/2006 | Bert et al. |
| 2007/0123065 A1 | 5/2007 | Rosenfeldt et al. |
| 2010/0151734 A1 | 6/2010 | Wu et al. |

OTHER PUBLICATIONS

International Search Report and Written Opinion for Application No. PCT/US2008/079429, mailed Feb. 12, 2009 in 13 pages.

International Written Opinion of the International Preliminary Examining Authority for Application No. PCT/US2008/079429, mailed Sep. 24, 2009 in 6 pages.

Notification of Transmittal of the International Preliminary report on Patentability for Application No. PCT/US2008/079429, mailed Dec. 3, 2009 in 12 pages.

U.S. Appl. No. 29/296,064, filed Oct. 12, 2007.

U.S. Appl. No. 29/296,067, filed Oct. 12, 2007.

U.S. Appl. No. 29/304,439, filed Feb. 29, 2008.

English translation of Japanese Office Action issued Sep. 27, 2012 in Japanese Patent Application No. JP 2010-529060.

* cited by examiner

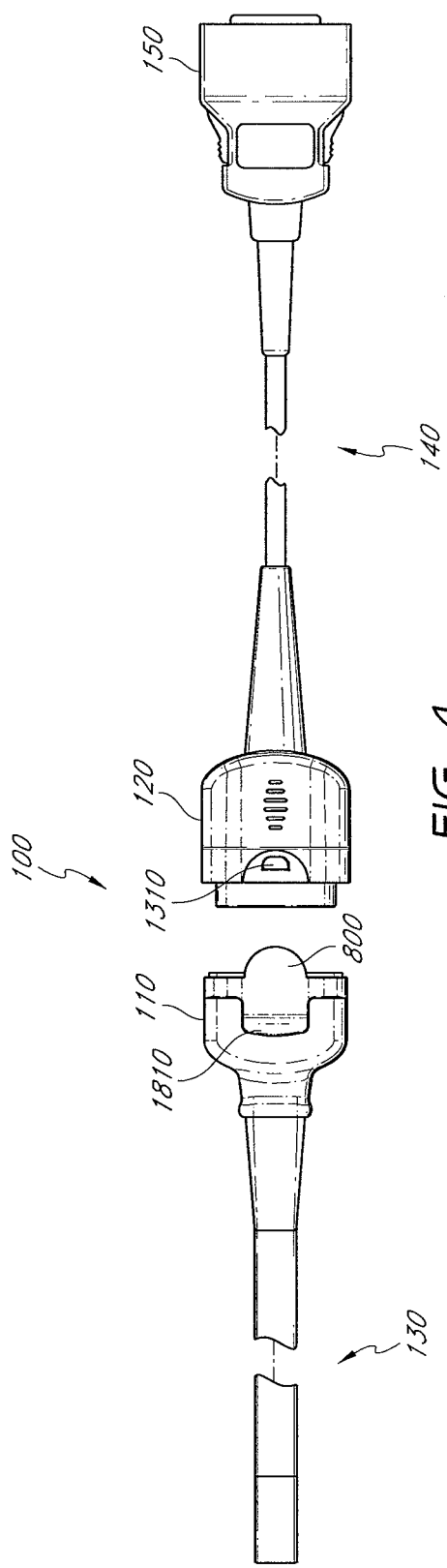
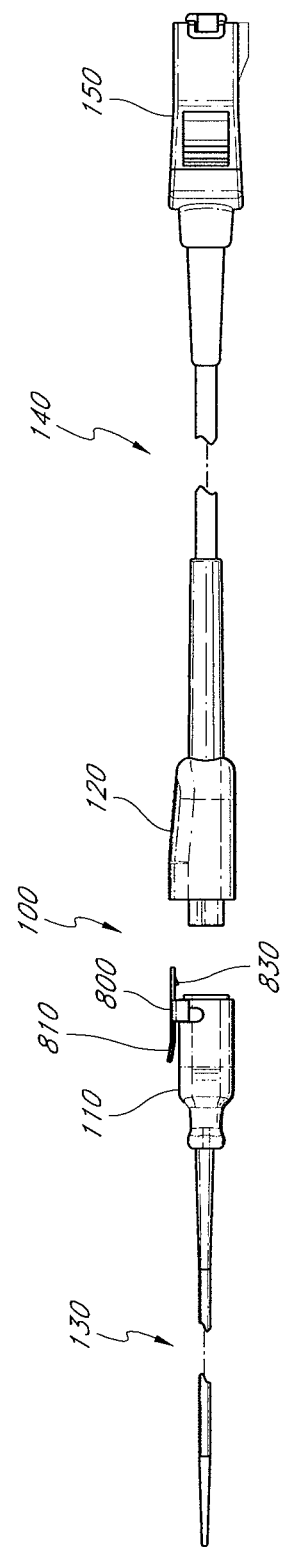
FIG. 4
FIG. 5

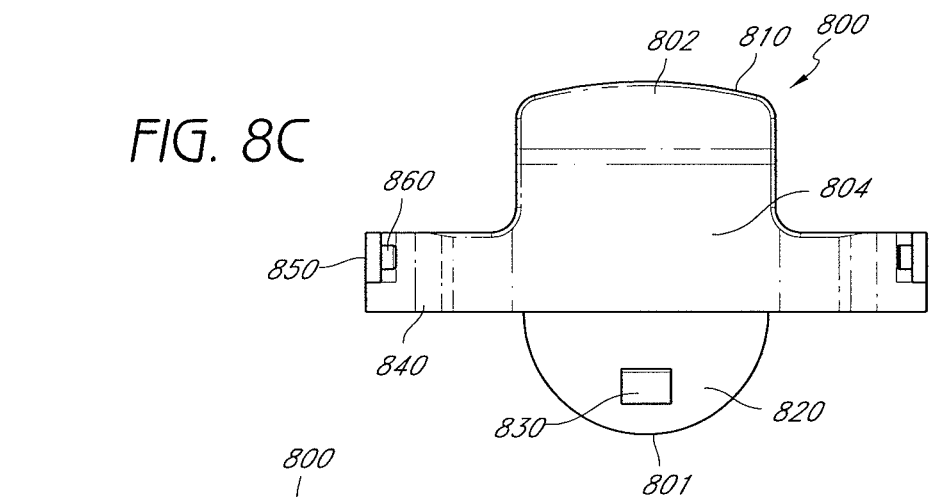
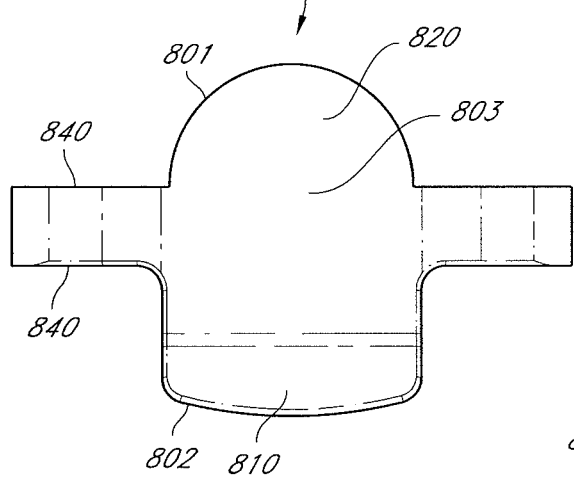
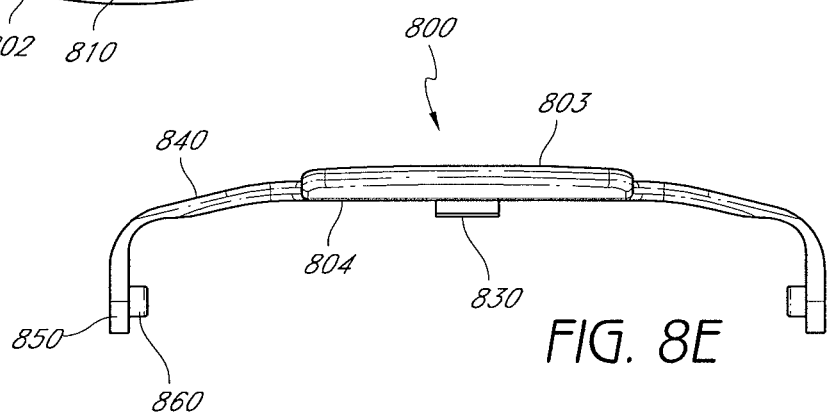
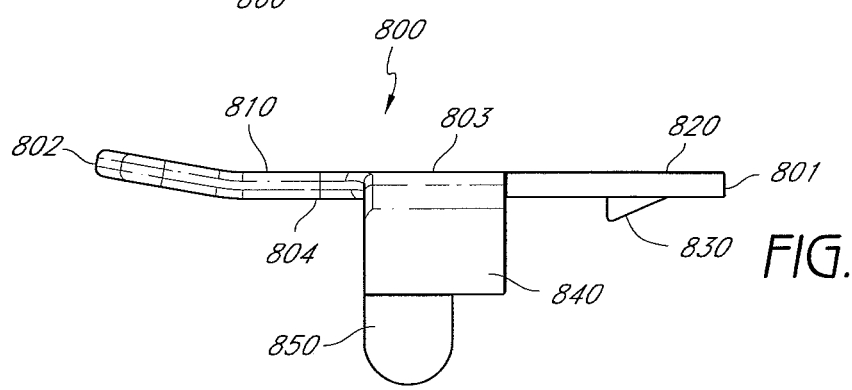

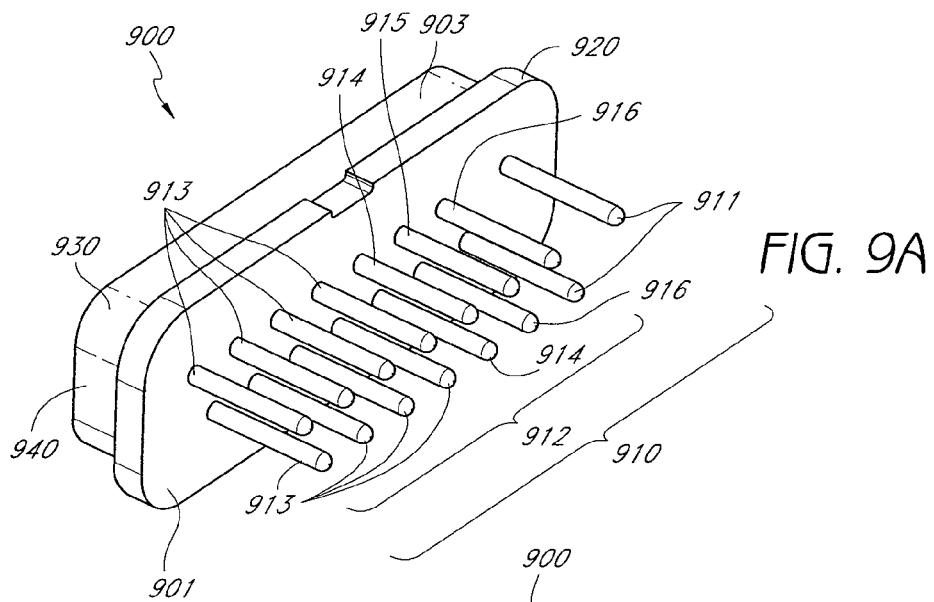
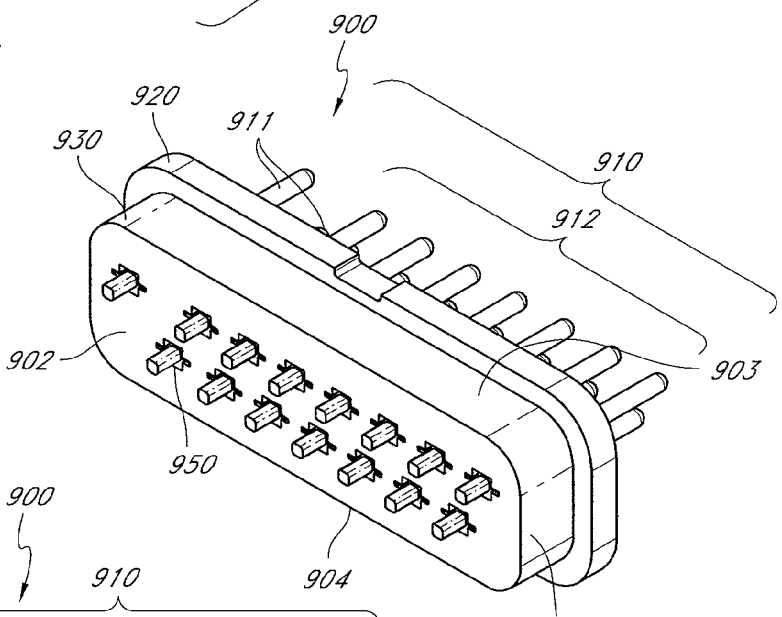
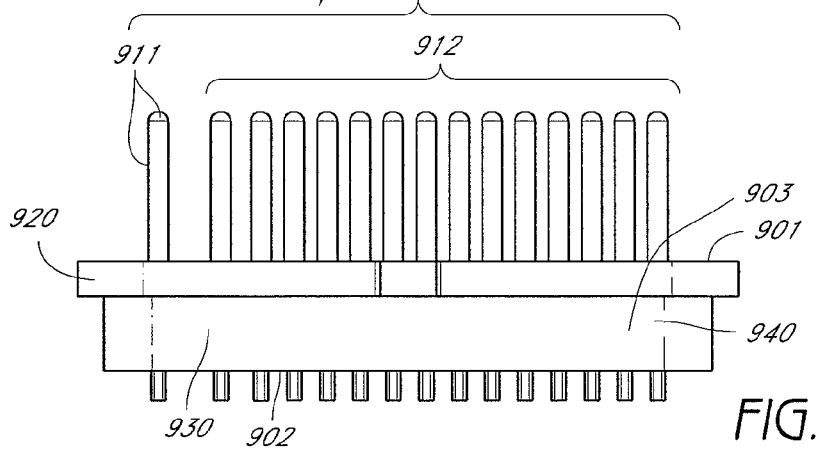
FIG. 9A
FIG. 9B
FIG. 9C

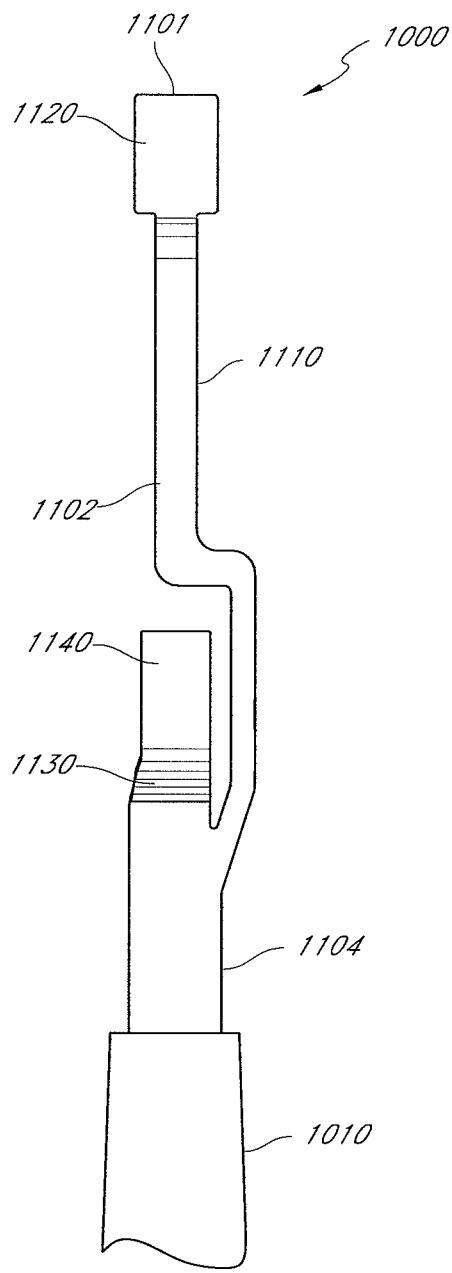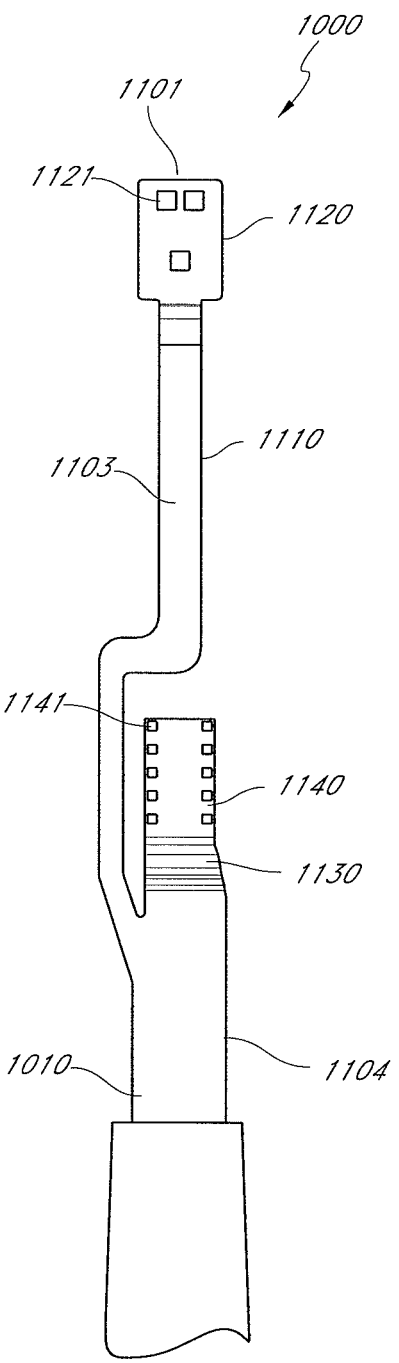
FIG. 11D
FIG. 11E

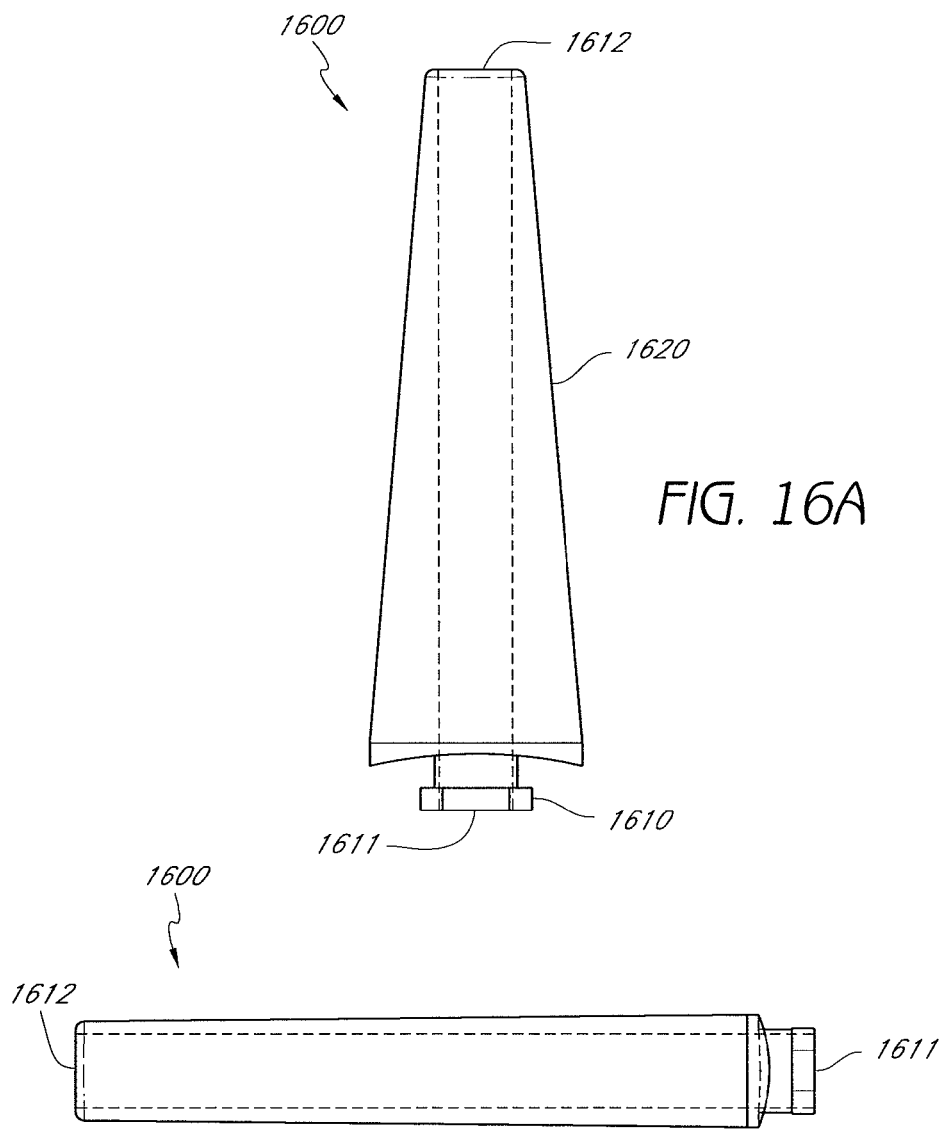
FIG. 16A
FIG. 16B
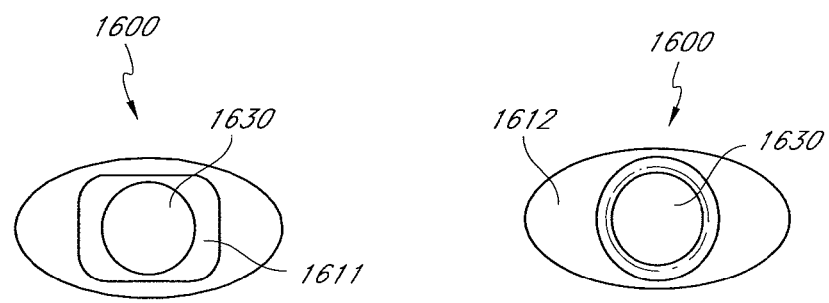
FIG. 16C
FIG. 16D

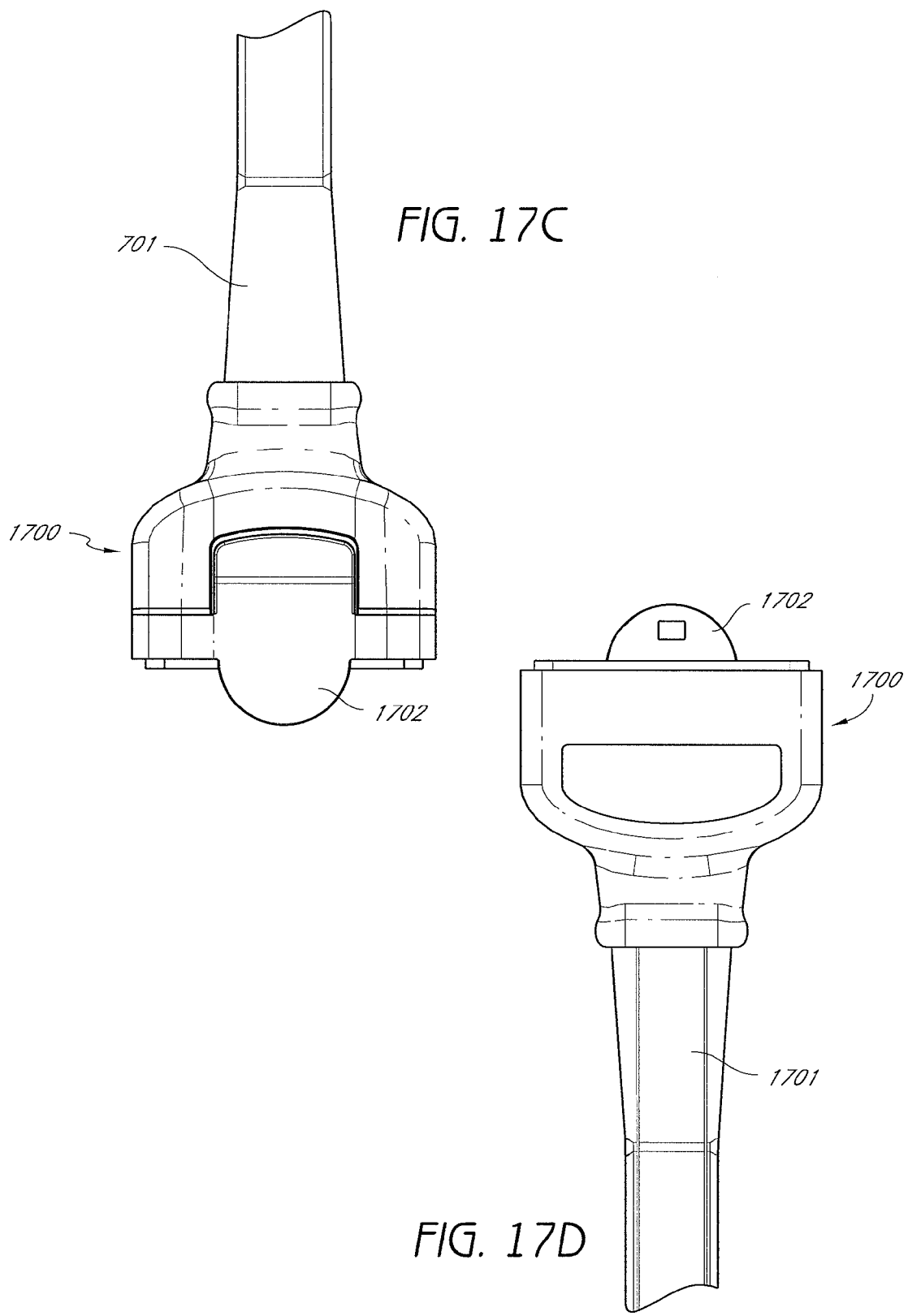

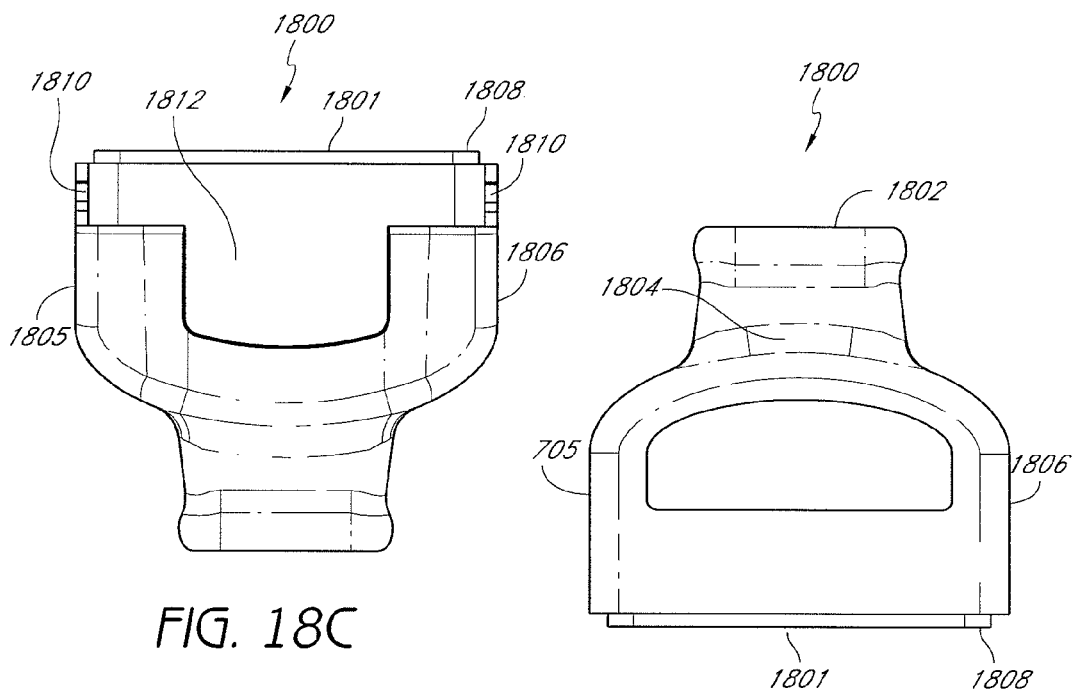
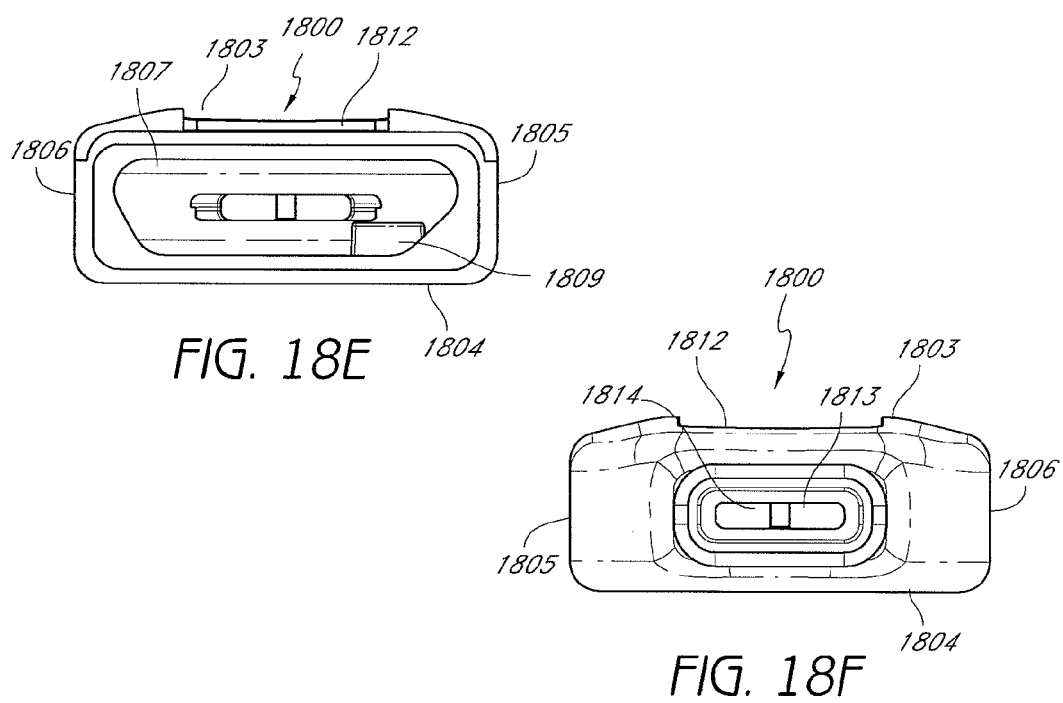

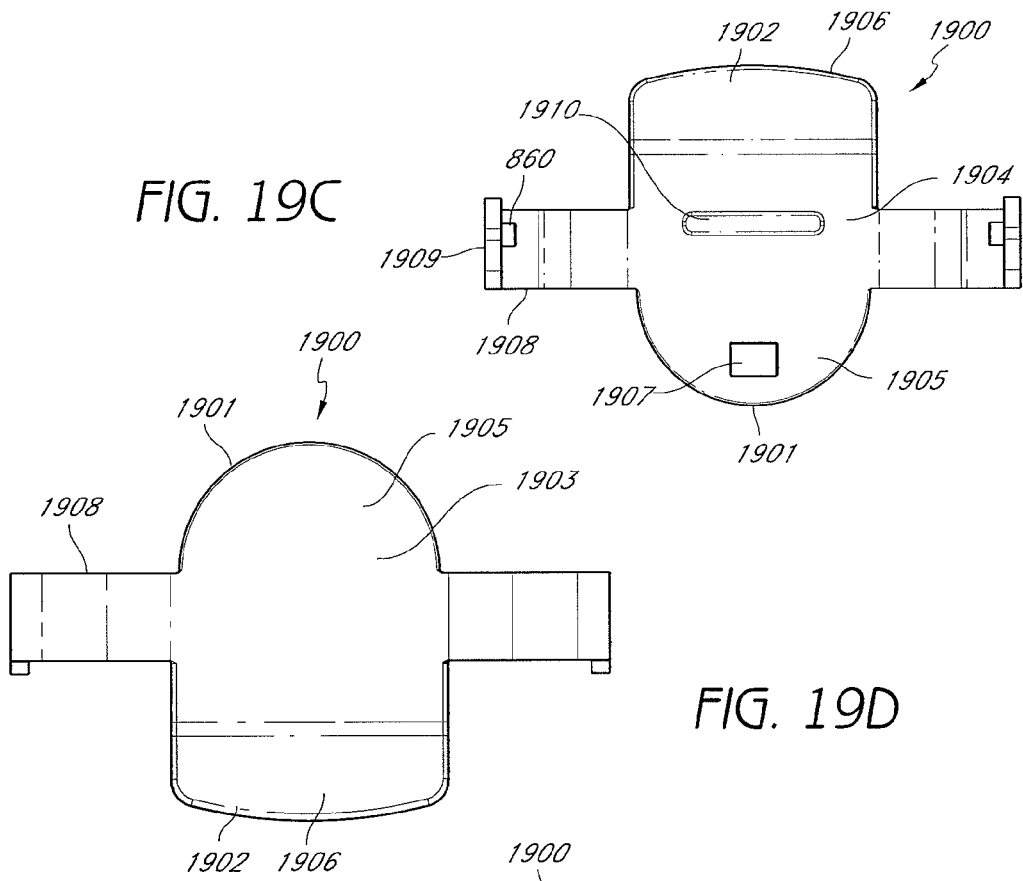
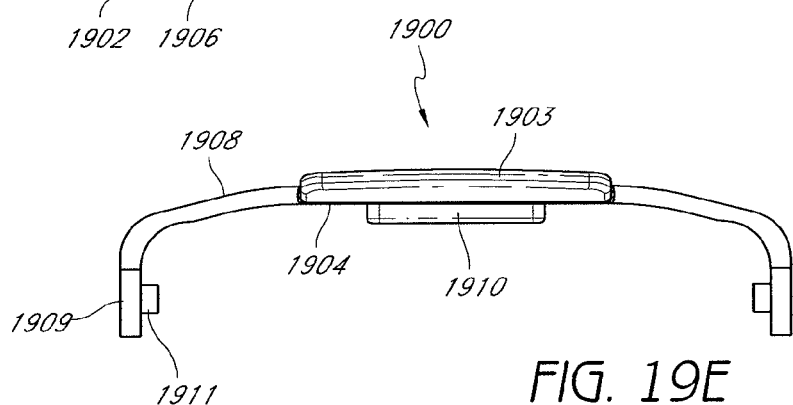
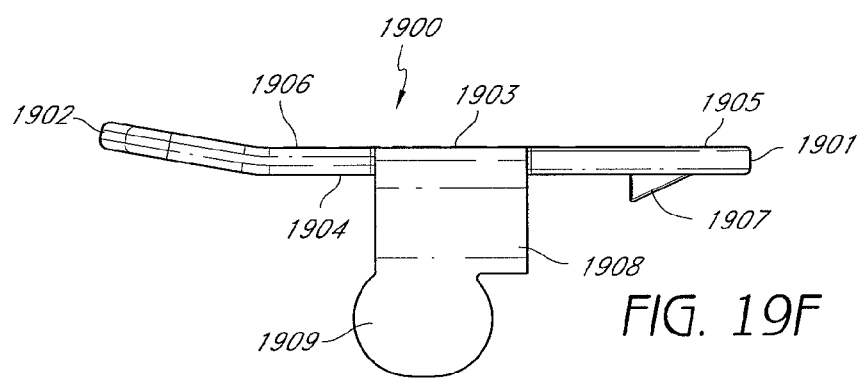

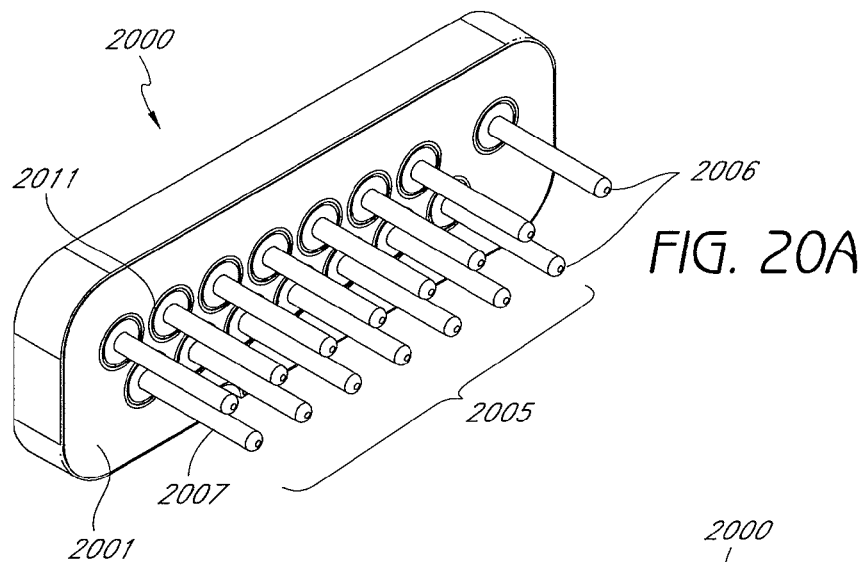
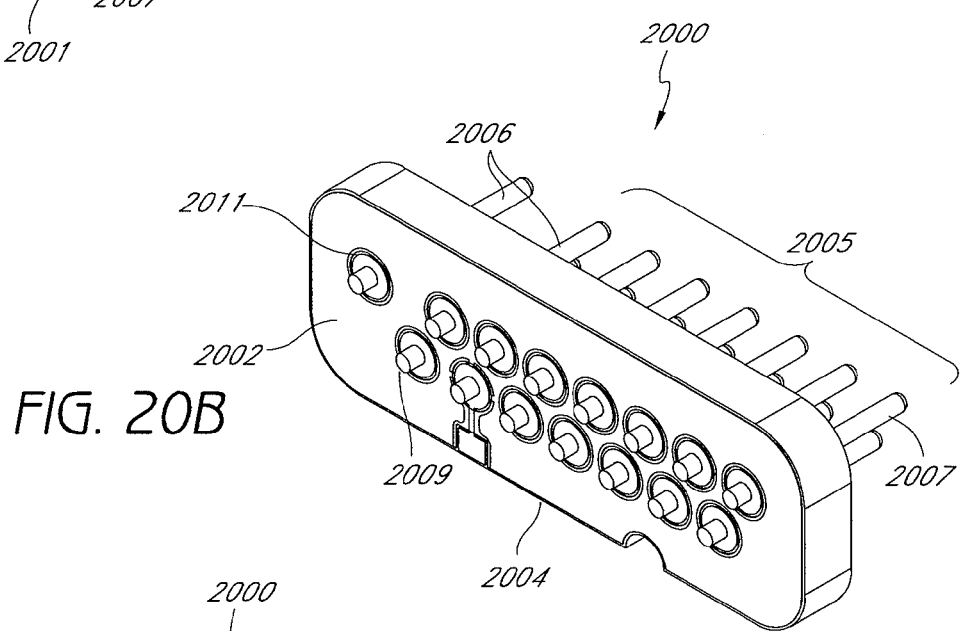
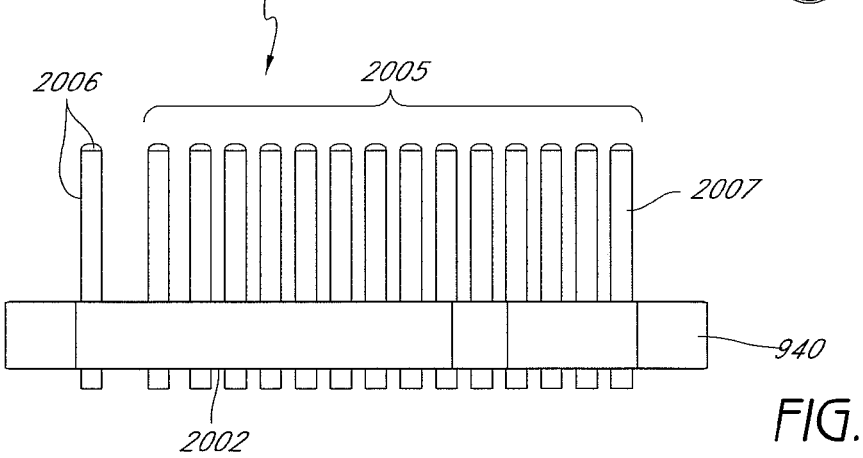

US 8,529,301 B2

SHIELDED CONNECTOR ASSEMBLY

RELATED CASES

The present application is a continuation of U.S. application Ser. No. 12/248,856, filed Oct. 9, 2008, entitled, "Connector Assembly with Reduced Unshielded Area," which claims priority benefit from U.S. Provisional Application No. 60/979,674, filed Oct. 12, 2007, entitled, "Connector Assembly," and from U.S. Provisional Application No. 61/032,936, filed Feb. 29, 2008, entitled, "Connector Assembly." The disclosures of each of the foregoing applications are hereby incorporated by reference herein.

The present disclosure is generally related to U.S. Provisional Application Ser. No. 60/846,260, filed Sep. 20, 2006, to U.S. patent application Ser. No. 11/858,818, filed Sep. 20, 2007, to U.S. Design patent application Ser. No. 29/296,064, filed Oct. 12, 2007, to U.S. Design patent application Ser. No. 29/296,067, filed Oct. 12, 2007 and to U.S. Design patent application Ser. No. 29/304,439, filed Feb. 29, 2008, which are incorporated herein by reference.

FIELD OF THE DISCLOSURE

The present disclosure is generally related to patient monitoring cable connector assemblies.

BACKGROUND OF THE DISCLOSURE

Pulse oximetry provides a noninvasive procedure for measuring the oxygen status of circulating blood and has gained rapid acceptance in a wide variety of medical applications, including surgical wards, intensive care and neonatal units, general wards, and home care and physical training. A pulse oximetry system generally includes a physiological sensor applied to a patient, a monitor, and a patient cable connecting the sensor and the monitor. The sensor has light emitters and a detector, which are attached to a tissue site, such as a finger. The patient cable transmits emitter drive signals from the monitor to the sensor where the emitters respond to the drive signals to transmit light into the tissue site. The detector is responsive to the emitted light after attenuation by pulsatile blood flowing in the tissue site. The detector outputs a detector signal to the monitor. The monitor processes the detector signal to provide a numerical readout of physiological parameters such as oxygen saturation ($SpO_2$) and pulse rate. Enhanced oximetry systems can also include a multiple parameter monitor and a multiple wavelength sensor that provide enhanced measurement capabilities, including, for example, the measurement of a multitude of blood constituents and related parameters in addition to oxygen saturation and pulse rate, such as, for example, carboxyhemoglobin (HbCO), methemoglobin (HbMet), total Hematocrit (Hct), oxygen concentrations, glucose concentrations or the like.

High fidelity pulse oximeters capable of reading through motion induced noise are disclosed in U.S. Pat. Nos. 6,770,028, 6,658,276, 6,157,850, 6,002,952 5,769,785, and 5,758,644, which are assigned to Masimo Corporation ("Masimo") and are incorporated by reference herein.

Pulse oximetry systems are often operated in highly fluid environments such as intensive care units. In such environments it is particularly advantageous for medical personnel to be able to connect sensors and patient cables with a strong connection, thereby possibly reducing a number of disconnects. For example, existing connector assemblies often utilize a hinged-plastic retainer, generally similar to a hood, to reduce accidental disconnects. The retainer often mechanically hinges from one side of a connector over a matable other side of the connector making mechanical disconnect very difficult without re-raising the hood. For example, typically the retainer attaches to the cable, in particular to a connector of a sensor.

SUMMARY OF THE DISCLOSURE

When the connection is subject to a threshold amount of stress, the retainer may become damaged. For example, a patient may jerk on the sensor accidentally, damaging the retainer. In other cases, hospital personnel may attempt to move the patient and leave the sensor connected, causing stress on the connection. In such cases, a user may replace the entire patient cable because of the damaged retainer. Accordingly a need exists to reduce costs associated with replacing cable. A connector assembly according to embodiments of the present disclosure is advantageously configured to allow a sensor connector to straightforwardly and efficiently join with and detach from a patient cable connector.

Further, embodiments of the connector assembly advantageously reduce un-shielded areas in an electrical connection between the sensor and the monitor. In addition, embodiments of the connector assembly advantageously increase the shielding of detector signals coming from the patient sensor to the monitor.

If a retainer is attached to a patient cable connector, a user may decide to replace the entire patient cable in the event of damage to the retainer. In many cases, patient cables are more expensive and generally less convenient to replace than patient sensors, which are often disposable.

BRIEF DESCRIPTION OF THE DRAWINGS

FIG. 4 is a top view of a connector assembly of FIG. 3;

FIG. 5 is a side view of a connector assembly of FIG. 3;

FIGS. 8A-F are top and bottom perspective, bottom, top, front and side views of a male sensor connector latching member, respectively, according to an embodiment of the disclosure;

FIGS. 9A-C are front perspective, back perspective and top views of a male sensor connector plug, respectively, according to an embodiment of the disclosure;

FIGS. 11A-E are perspective, left side, right side, top and bottom views, respectively, of the sensor end of a flex circuit, according to an embodiment of the detector;

FIGS. 16A-D are top cross-sectional, side, front and back views of a strain relief, respectively, according to an embodiment of the disclosure;

FIGS. 17A-F are perspective, side, top, bottom, front and back views of a male sensor connector, respectively, of the connector assembly according to another embodiment of the disclosure;

FIGS. 18A-F are perspective, side, top, bottom, front and back views of a shell of the male sensor connector of FIG. 17, respectively;

FIGS. 19A-F are top and bottom perspective, bottom, top, front and side views of a male sensor connector latching member, respectively, according to another embodiment of the disclosure;

FIGS. 20A-C are front perspective, back perspective and top views of a male sensor connector plug, respectively, according to another embodiment of the disclosure;

DETAILED DESCRIPTION OF THE PREFERRED EMBODIMENT

Figure 1:
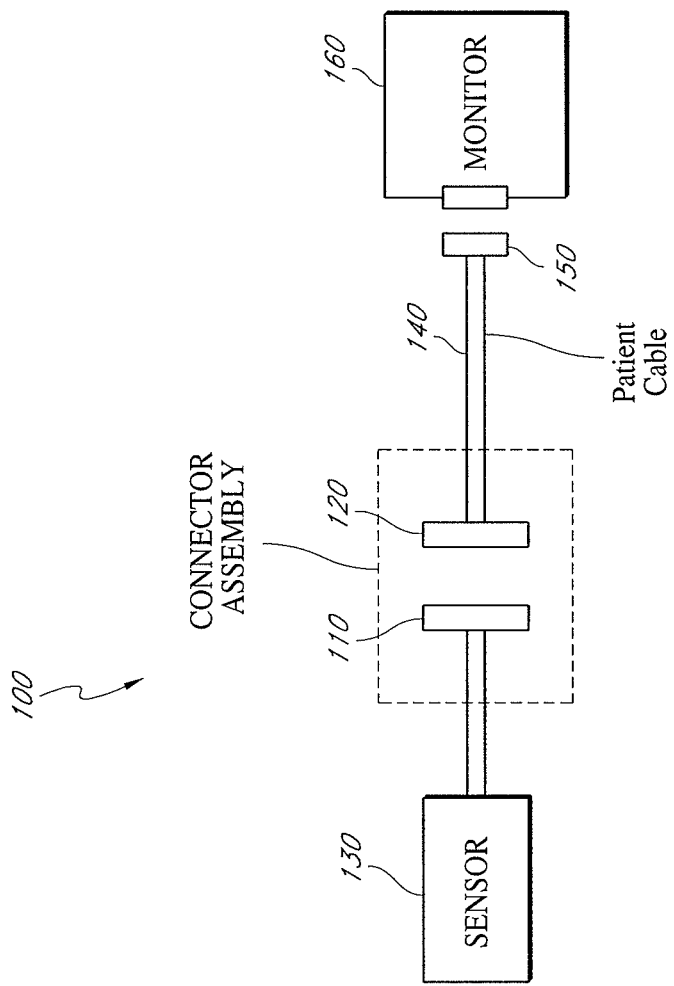
FIG. 1 is a general block diagram of a connector assembly utilized by a patient monitoring system.

FIG. 1 generally illustrates a connector assembly 100 as part of a patient monitoring system. The connector assembly 100 allows a sensor 130 to communicate with a monitor 160 via a patient cable 140 including wires and/or conductors that interconnect a patient cable connector 120 and a monitor connector 150. The connector assembly 100 includes a sensor connector 110 and the patient cable connector 120 and, advantageously, allows for relatively straightforward and efficient connection and separation of a sensor 130 from a patient cable 140. For example, the sensor 130 and patient cable 140 can be separated relatively straightforwardly and efficiently by a user, such as, for example, by single-handed separation. In various embodiments, the patient cable connector accepts different types of sensors and sensor configurations. For example, in one embodiment, the patient cable connector 120 accepts a wide variety of standard $SpO_2$ sensors. In another embodiment, the patient cable connector 120 accepts a multiple wavelength sensor, such as, for example, a 3, 8, 16 or more or other numbered wavelength sensor. In another embodiment, for example, the patient cable connector 120 accepts both a standard $SpO_2$ connector and a multiple wavelength sensor.

Figure 2A:
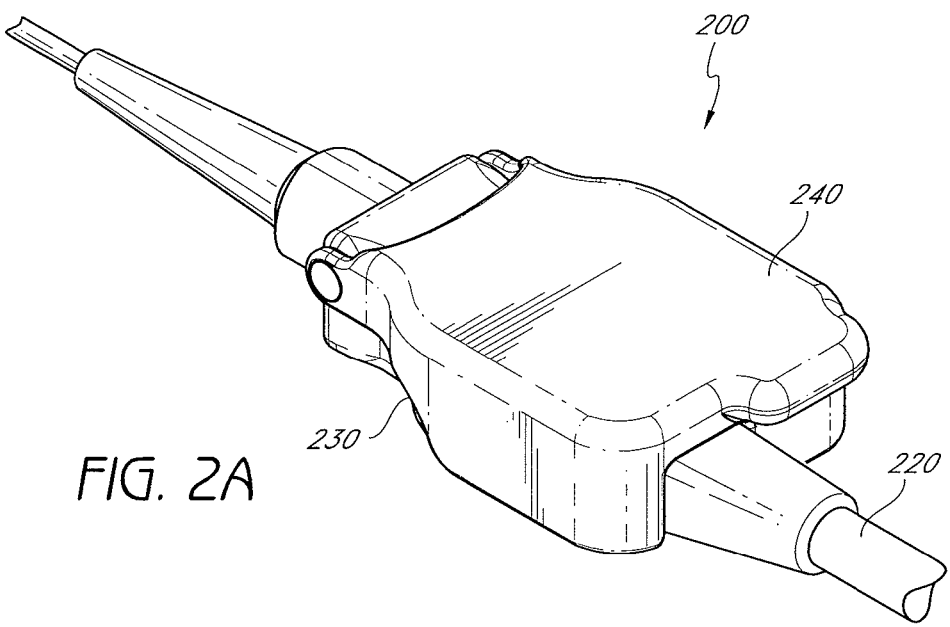
FIGS. 2A-D are perspective, top, side retainer hinged-open and side retainer hinged-closed views, respectively, of a connector assembly utilizing a hinged retainer latch mechanism.
Figure 2B:
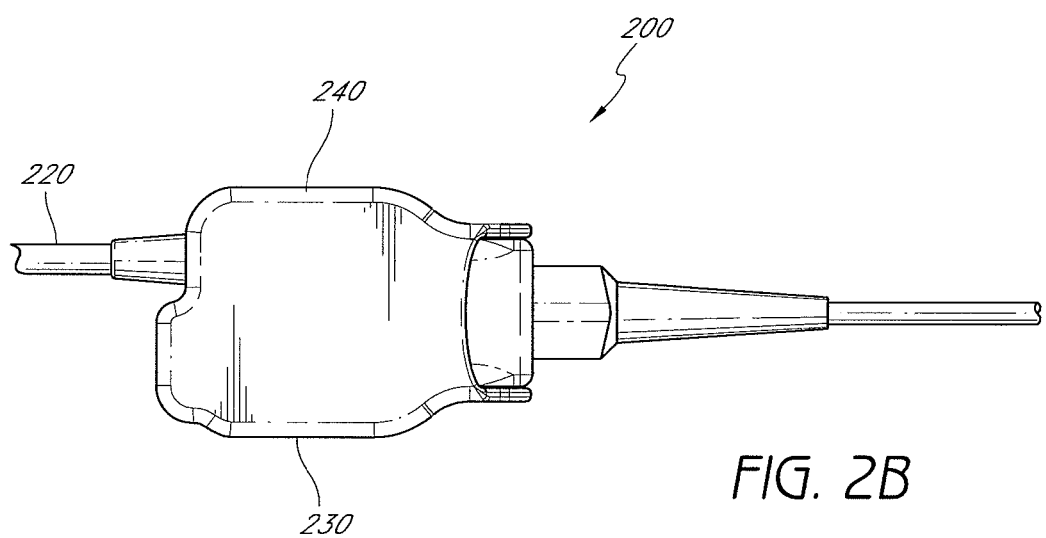
Figure 2C:
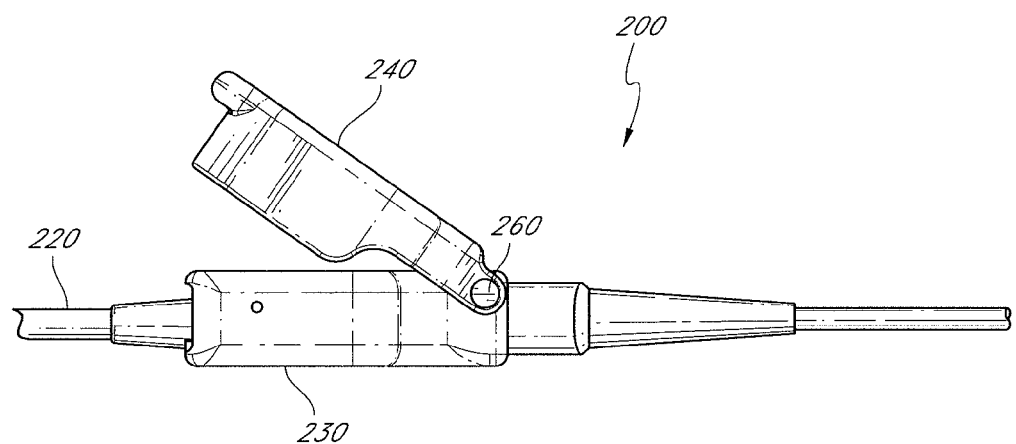
Figure 2D:
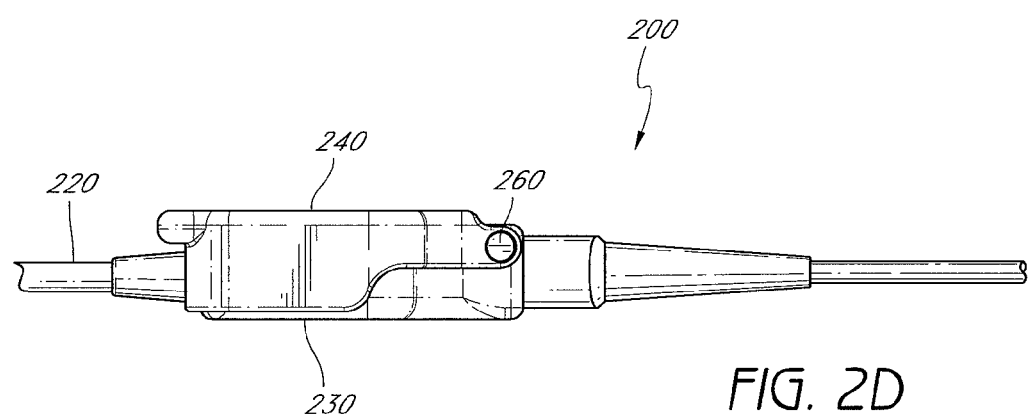

FIGS. 2A-D generally illustrate a connector assembly 200. A sensor connector 220 is connected to a patient cable connector 230. A retainer 240 is rotatable about an axis 260 and is movable between a closed position (FIGS. 2A-B and FIG. 2D) and an open position (FIG. 2C). In the open position, the retainer 240 allows for the sensor connector 220 to be inserted into or removed from the patient cable connector 230. In the closed position, the retainer 240 mechanically impedes the sensor connector 220 from inadvertently disconnecting. Generally, the process of joining the connectors consists of attaching the connectors and closing the retainer to secure or substantially secure the connection and reduce accidental disconnects. In some assemblies, the retainer 240 snaps into a locked position. The process of separating the connectors consists of hinging the retainer 240 open and disengaging the connectors 220, 230. Generally, this process employs two hands.

Figure 3:
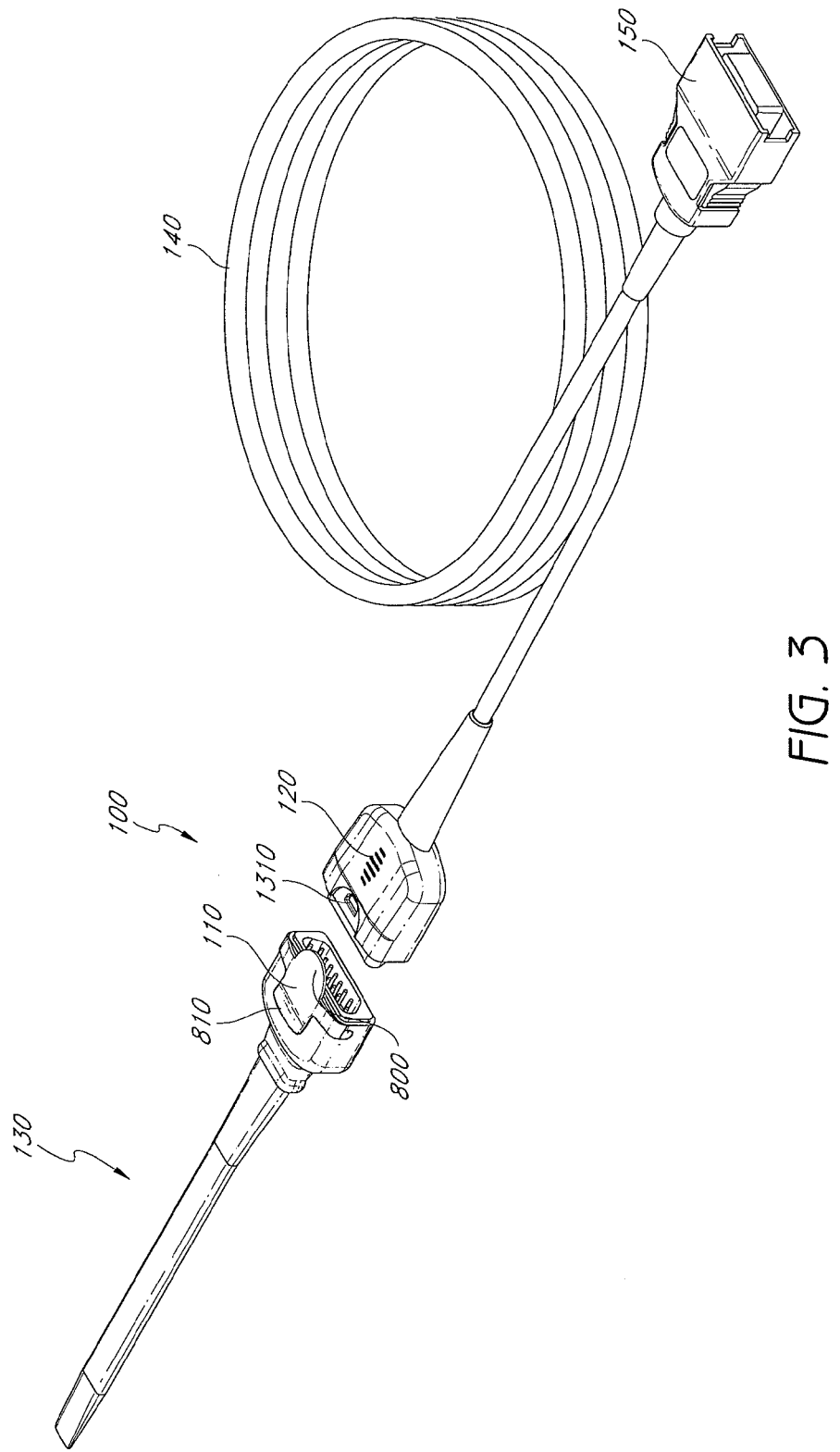
FIG. 3 is a perspective view of a connector assembly according to an embodiment of the disclosure.
Figure 6A:
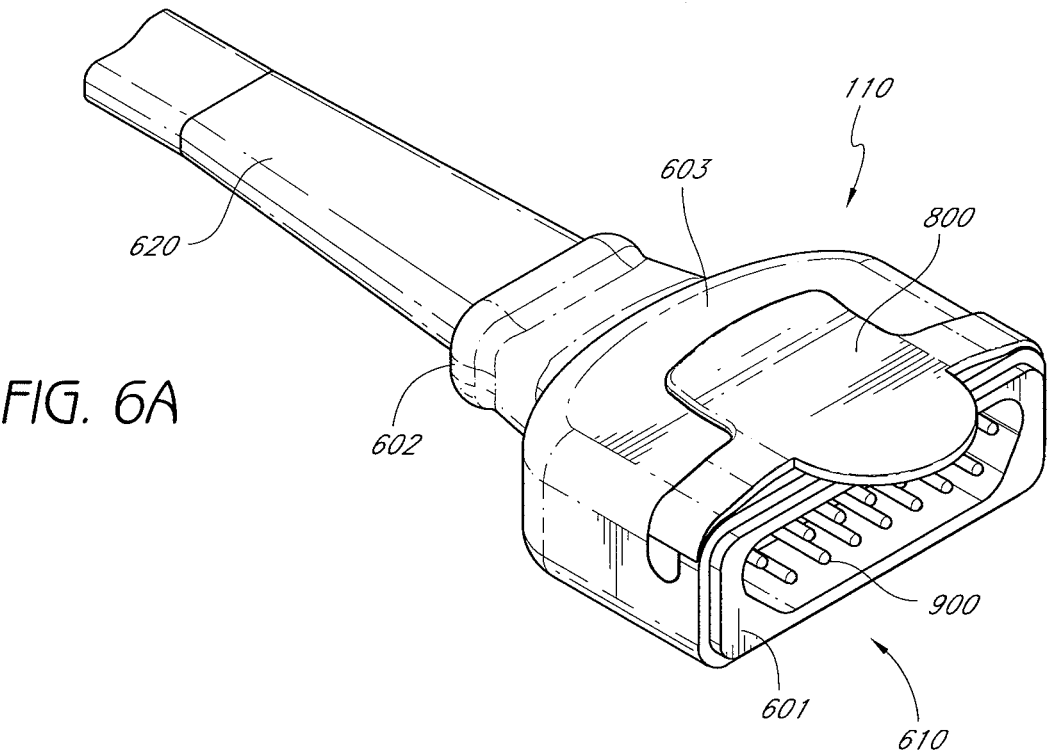
FIGS. 6A-F are perspective, side, top, bottom, front and back views of a male sensor connector, respectively, of the connector assembly of FIG. 3.
Figure 6B:
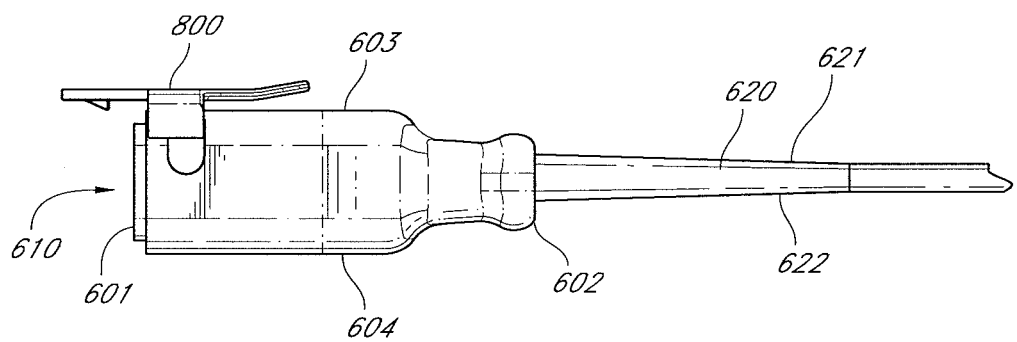
Figure 6C:
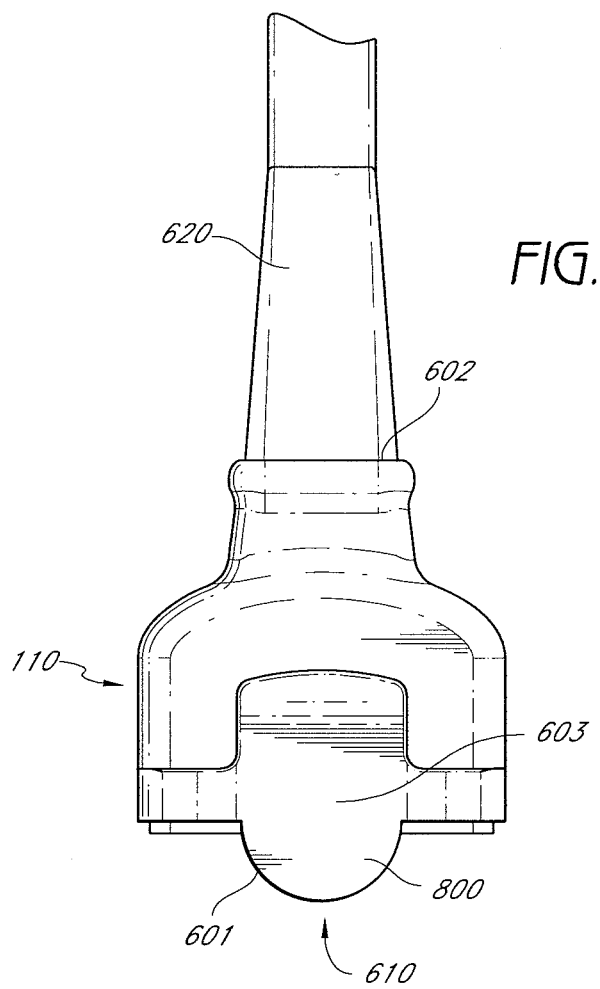
Figure 6D:
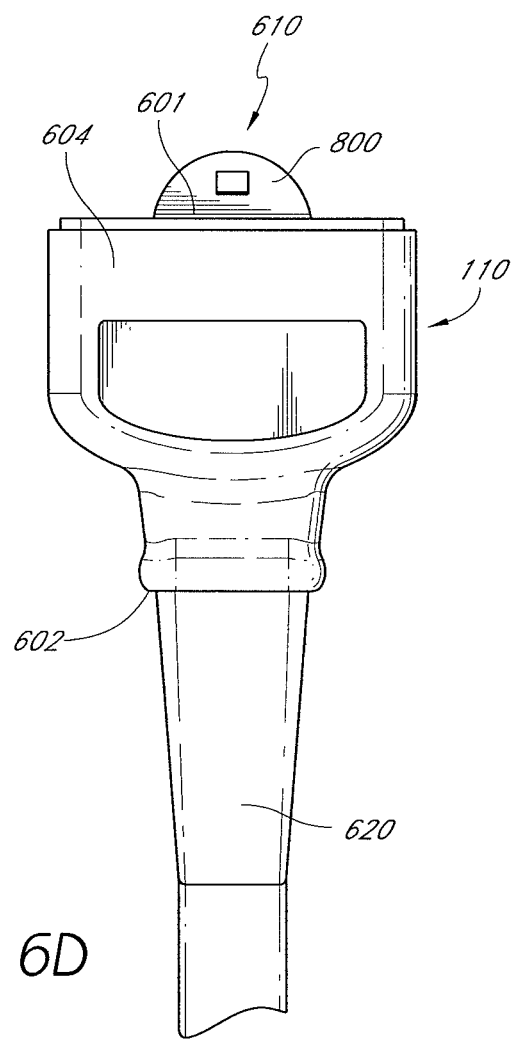
Figure 6E:
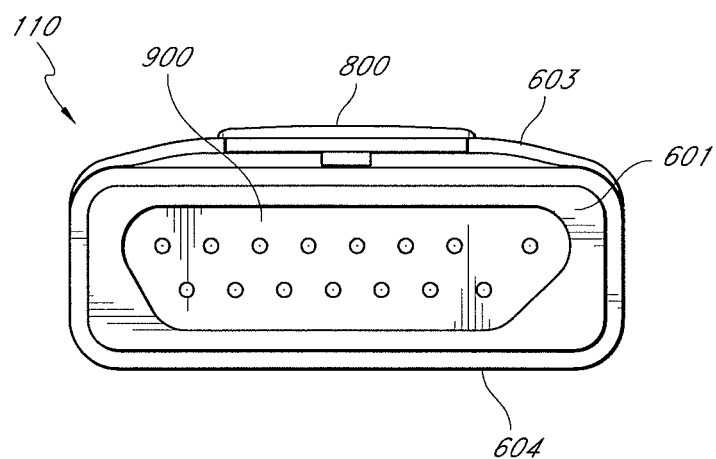
Figure 6F:
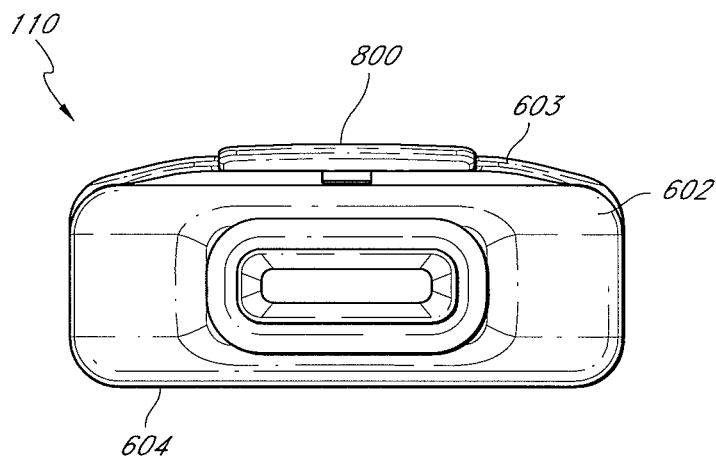
Figure 7A:
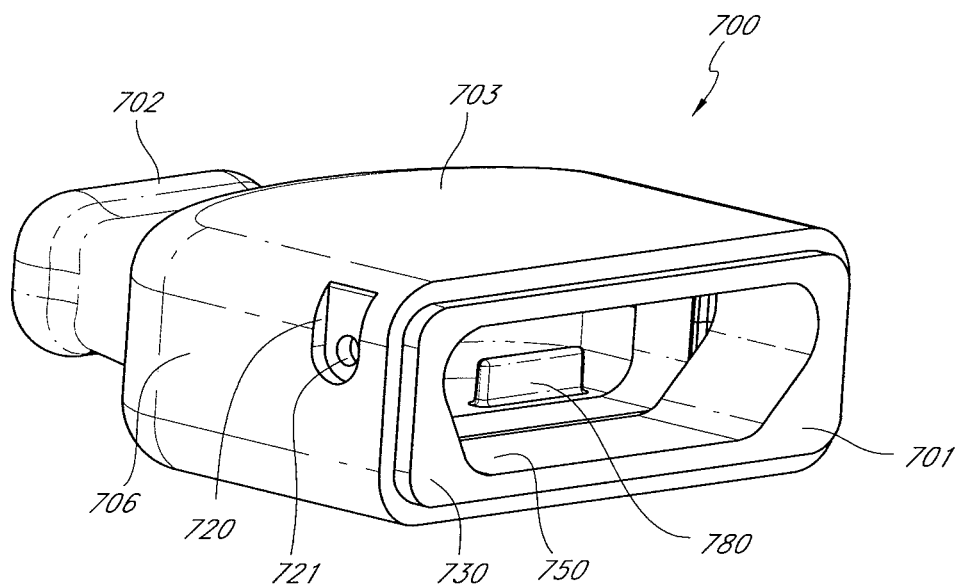
FIGS. 7A-F are perspective, side, top, bottom, front and back views of a shell of the male sensor connector of FIG. 6, respectively.
Figure 7B:
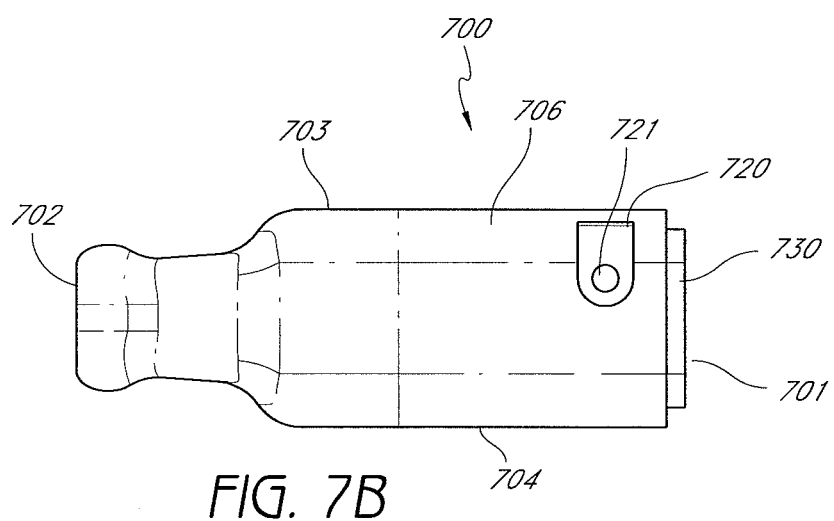
Figure 7C:
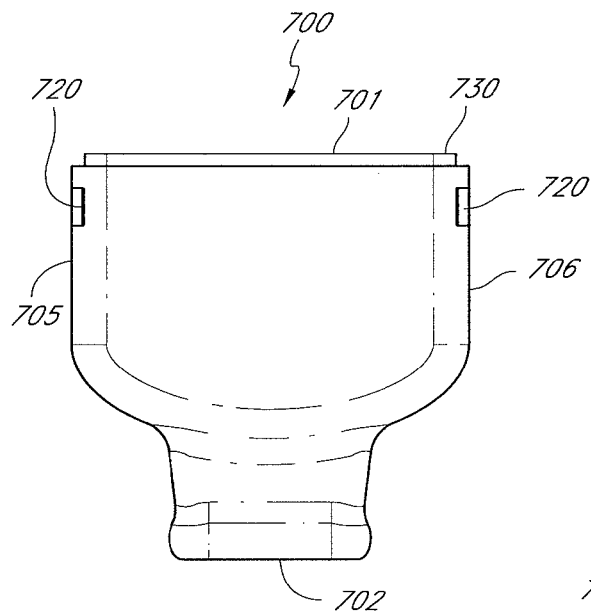
Figure 7D:
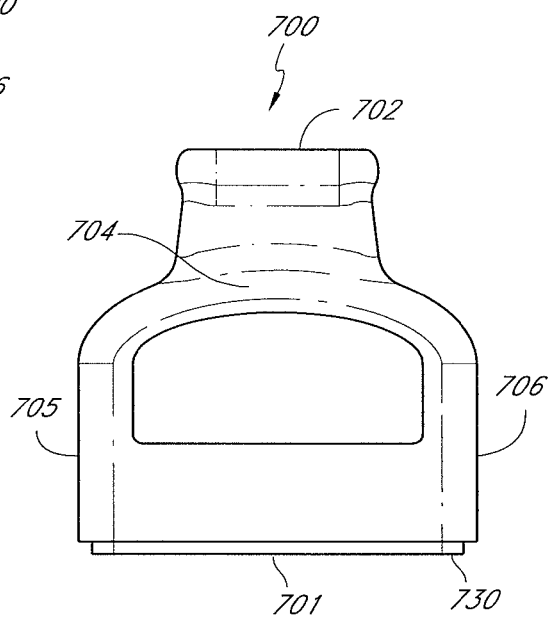
Figure 7E:
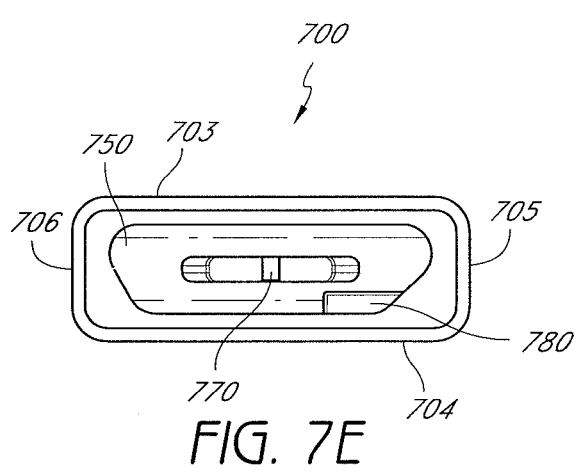
Figure 7F:
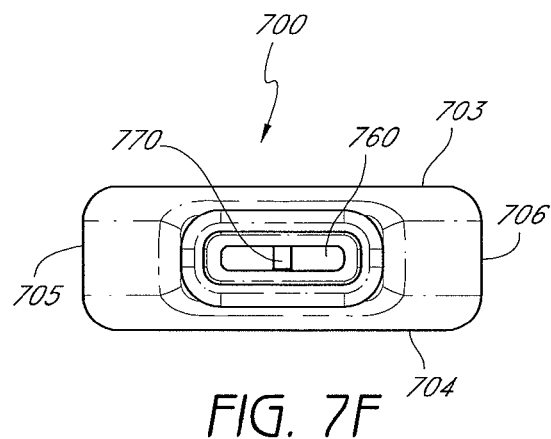
Figure 8A:
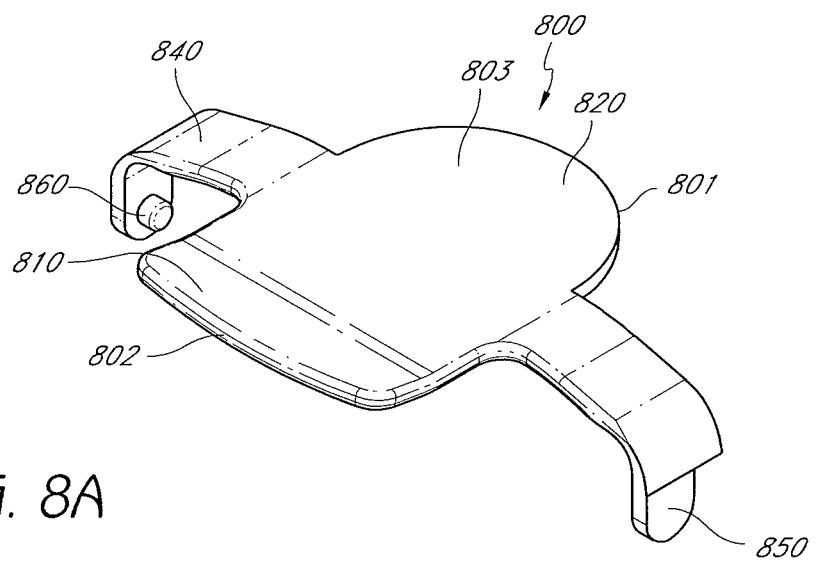
Figure 8B:
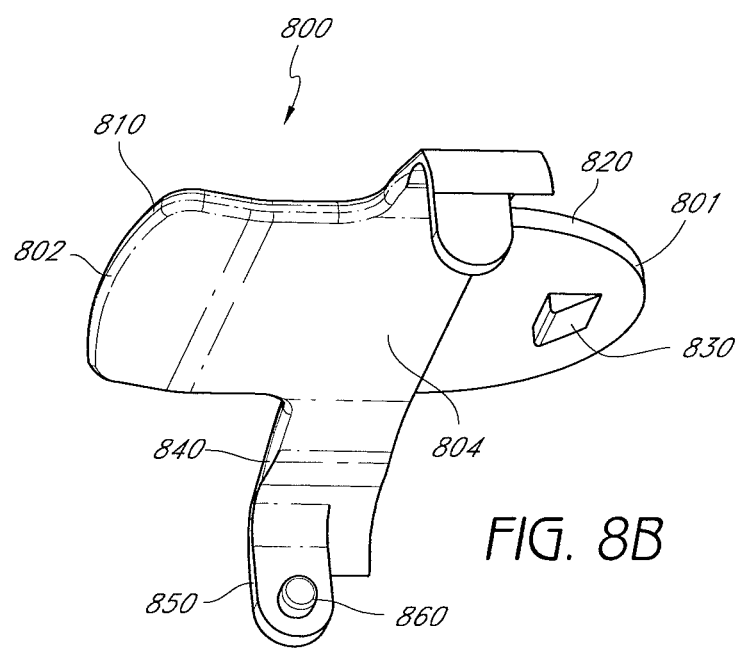
Figure 10A:
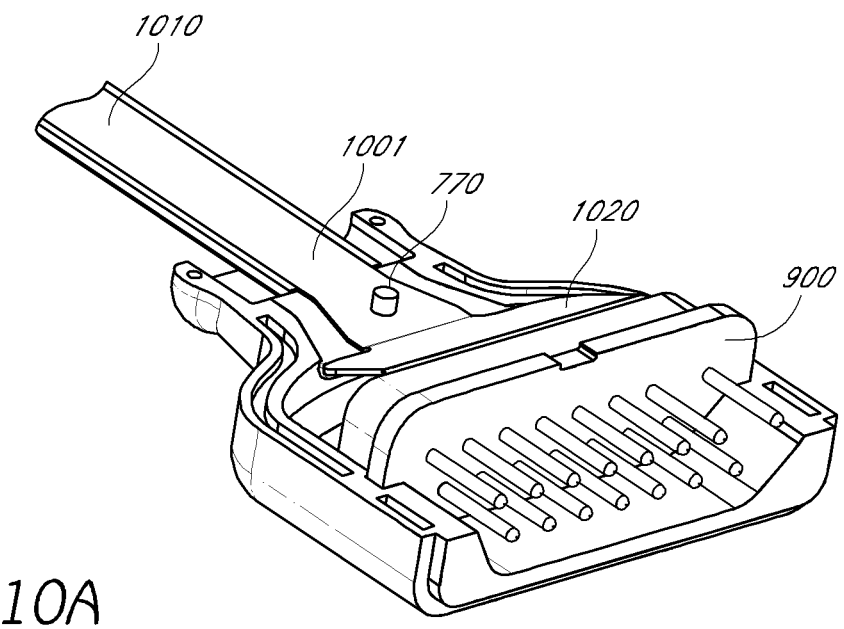
FIGS. 10A-E are perspective exploded, bottom perspective, side, top and bottom views, respectively, of the connector end of a flex circuit, according to an embodiment of the disclosure.
Figure 10B:
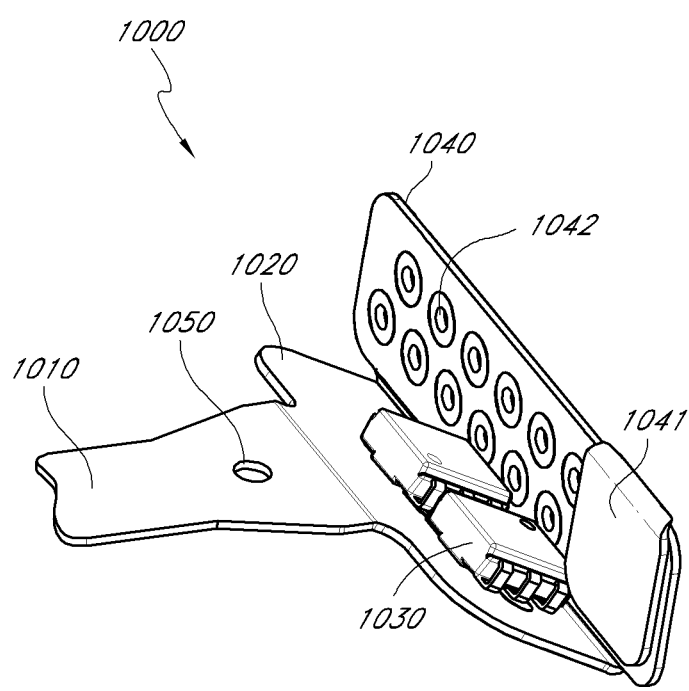
Figure 10C:
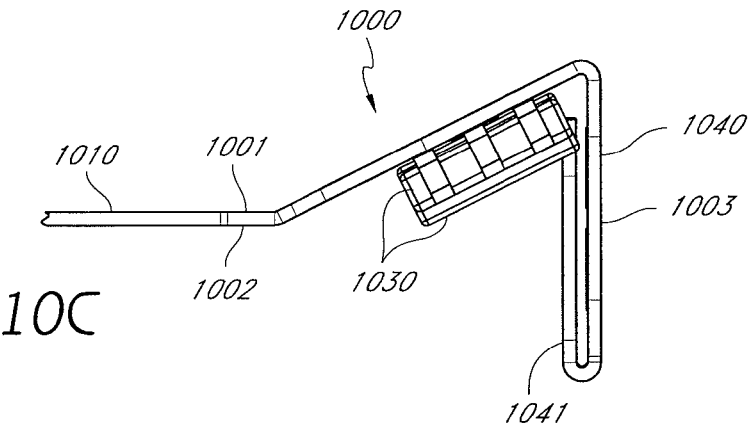
Figure 10D:
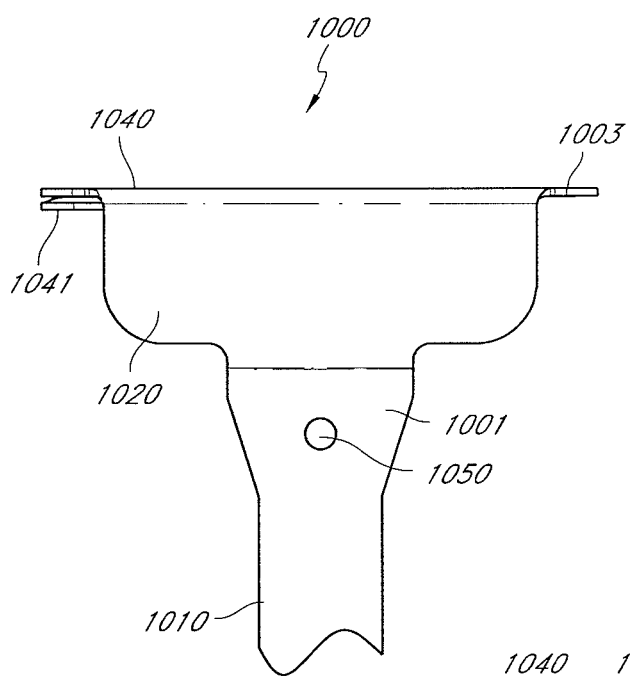
Figure 10E:
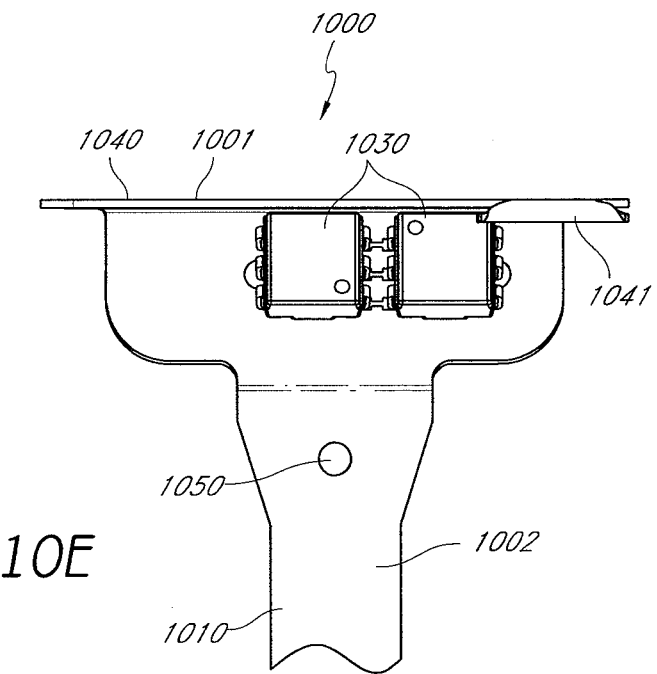
Figure 11A:
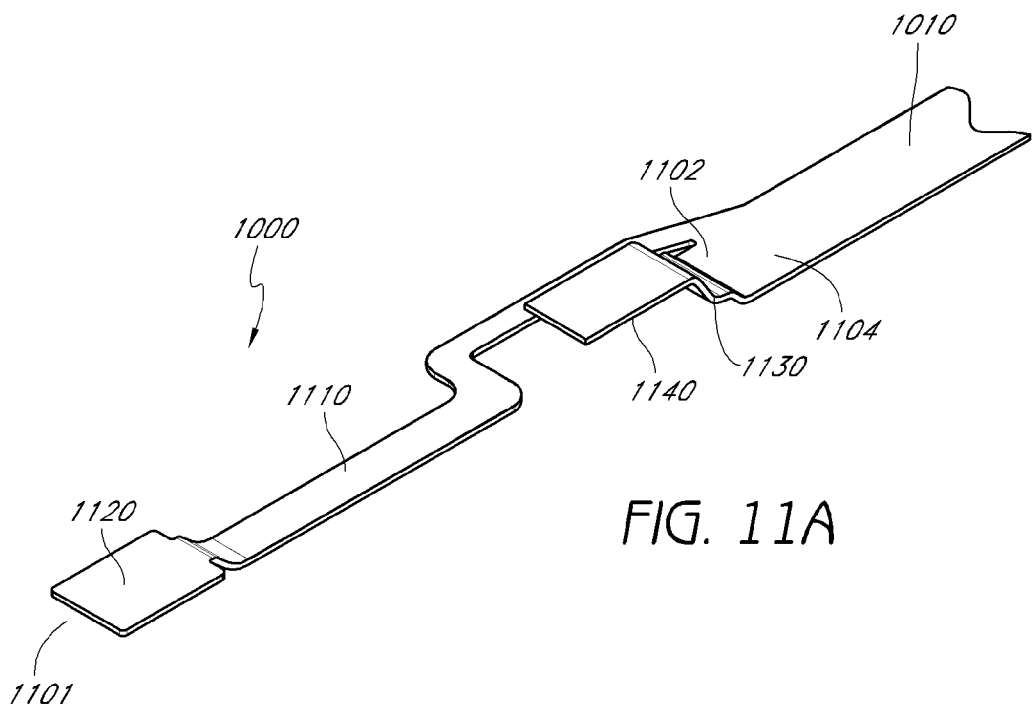
Figure 11B:
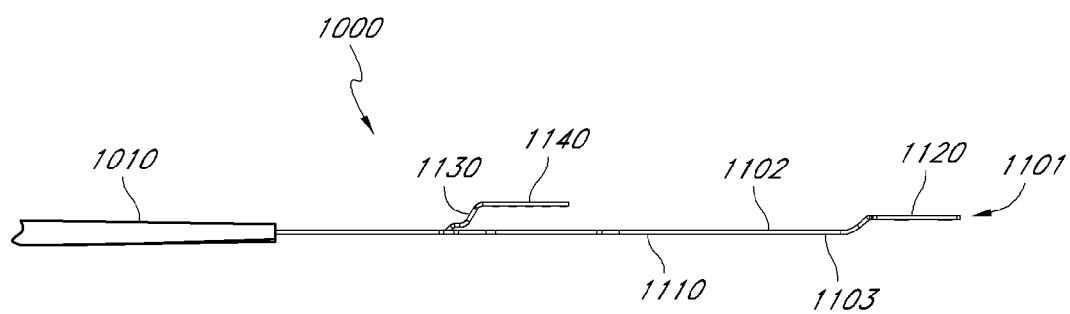
Figure 11C:
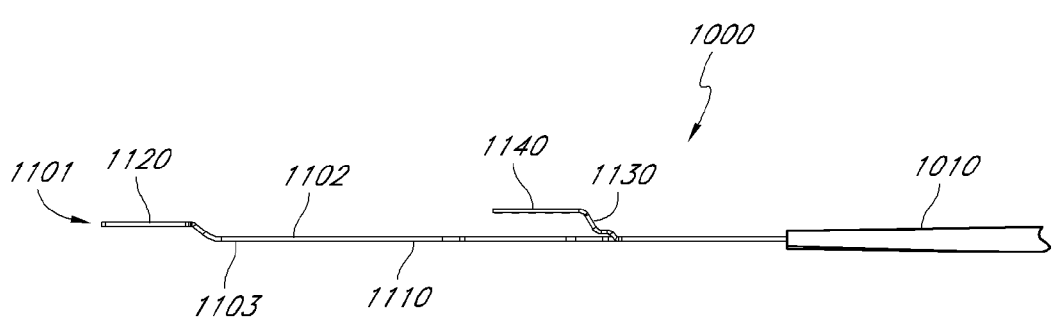
Figure 12A:
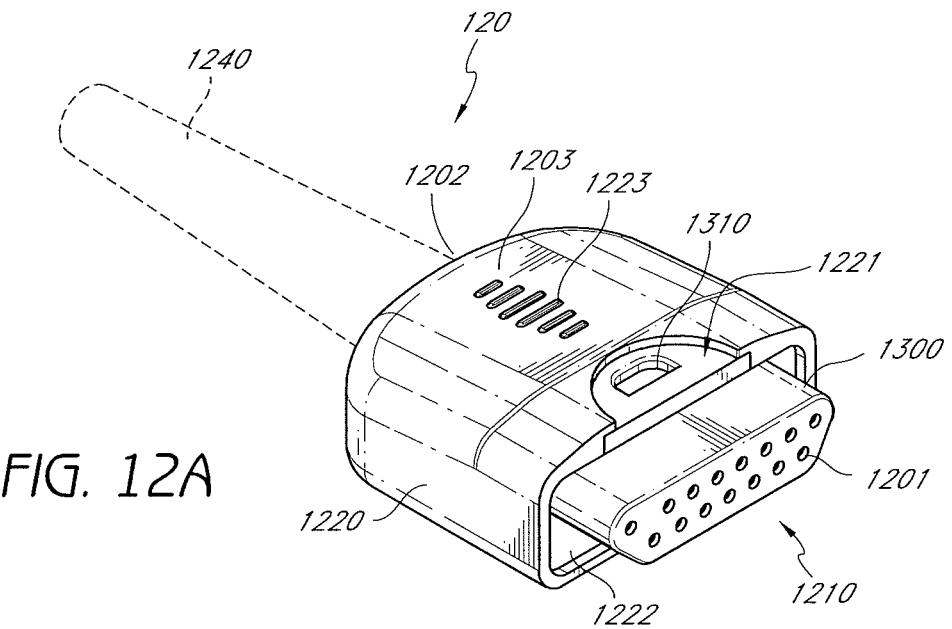
FIGS. 12A-F are perspective, side, top, bottom, front and back views of a female patient cable connector, respectively, of the connector assembly of FIG. 3.
Figure 12B:
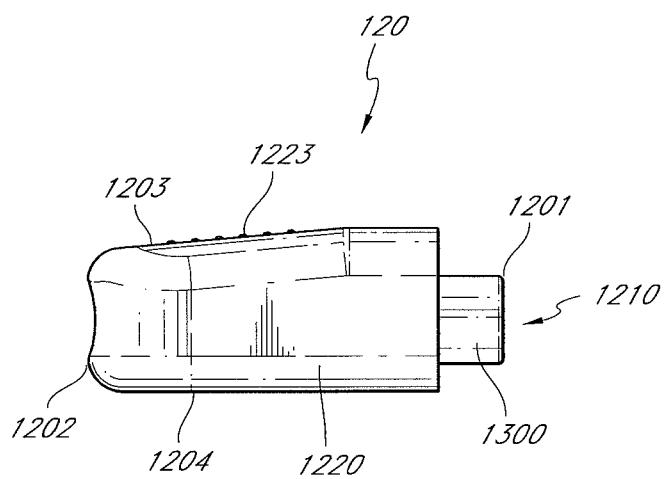
Figure 12C:
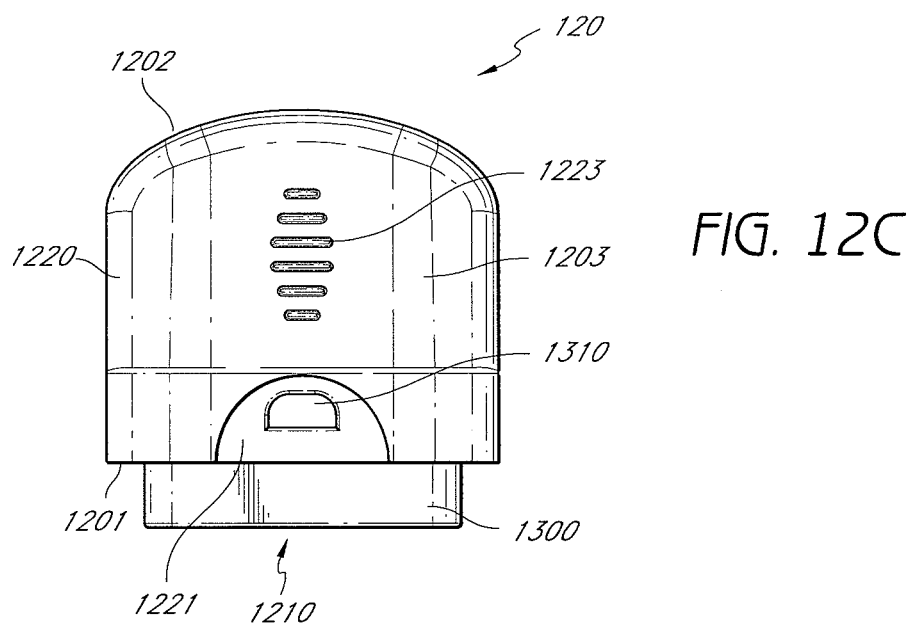
Figure 12D:
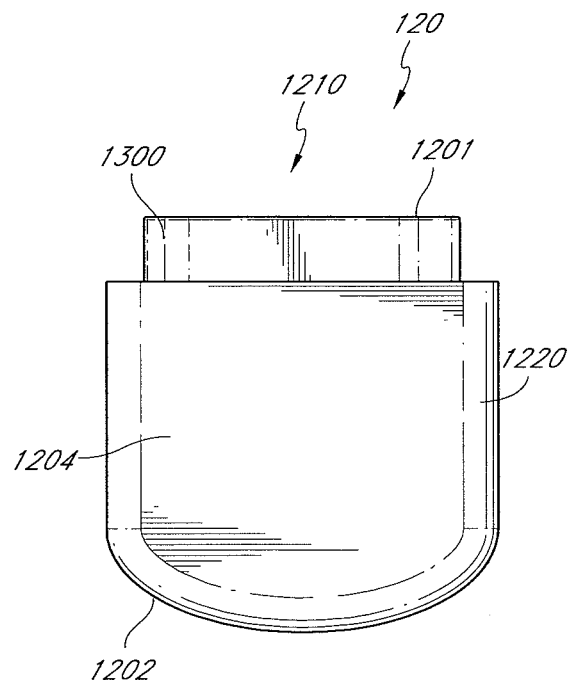
Figure 12E:
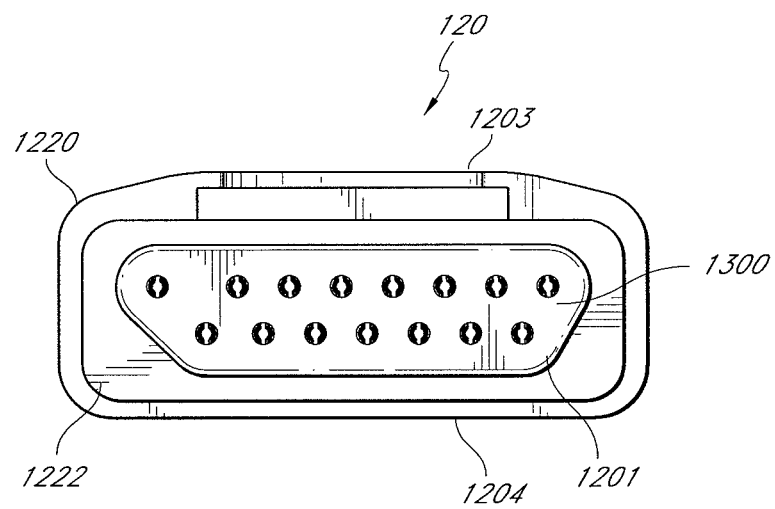
Figure 12F:
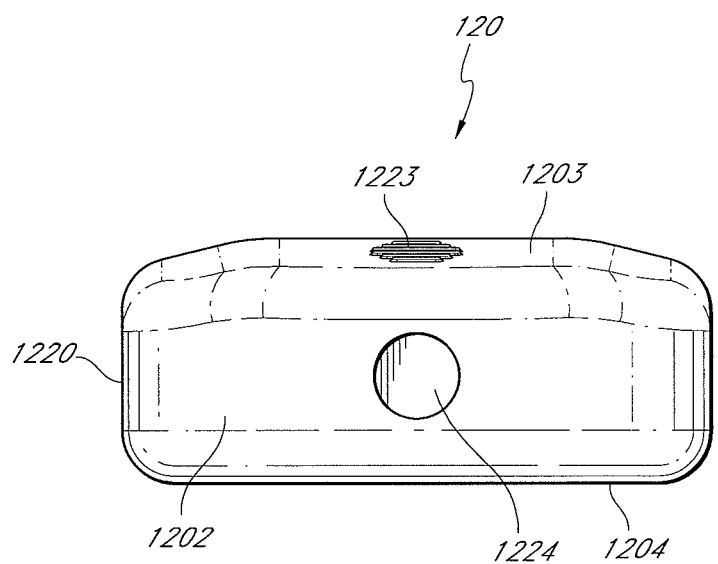
Figure 13A:
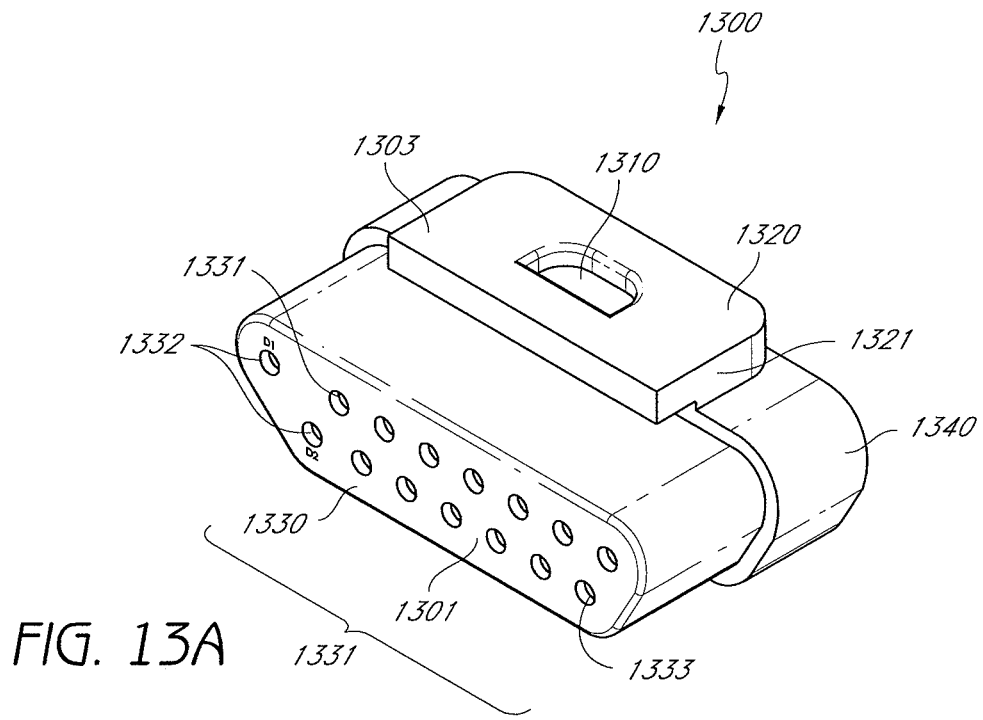
FIGS. 13A-E are front and back perspective, top, back and side views of a socket of the female patient cable connector of FIG. 12, respectively.
Figure 13B:
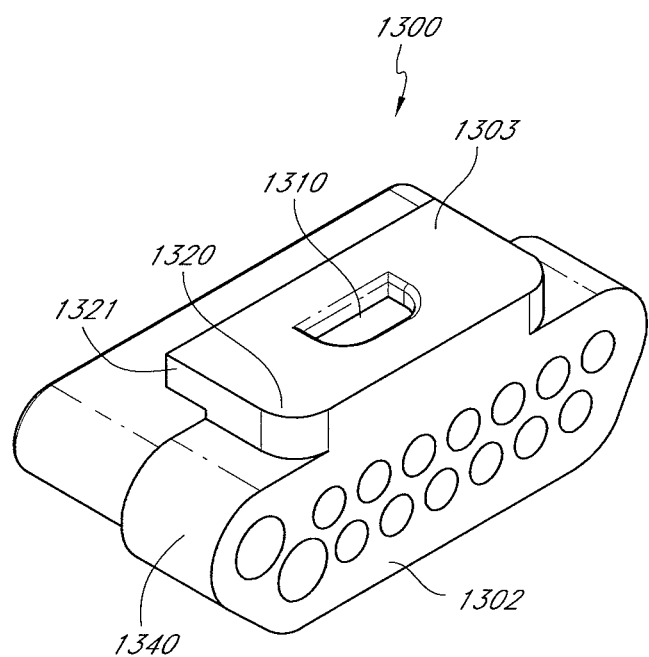
Figure 13C:
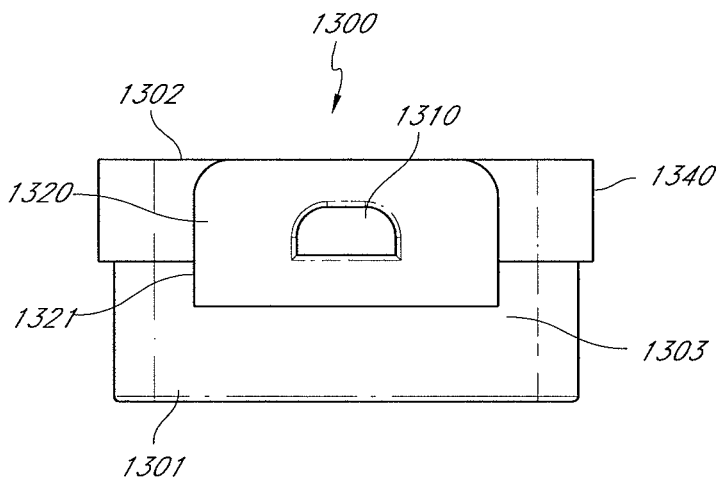
Figure 13D:
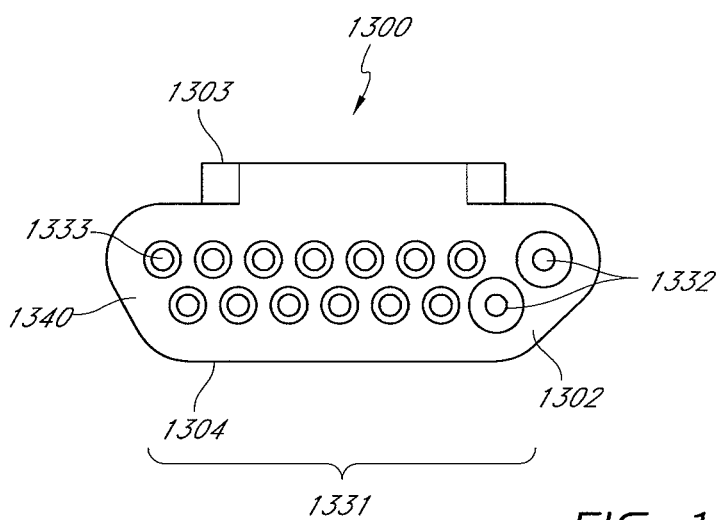
Figure 13E:
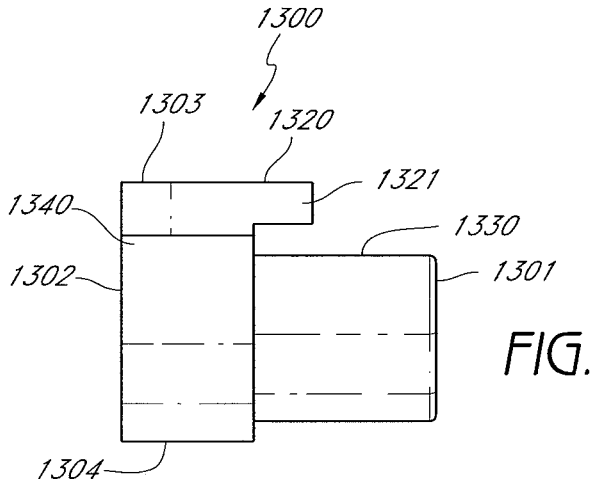

FIGS. 3-5 illustrate one embodiment of a connector assembly 100 having a multiple wavelength sensor 130. In the illustrated embodiment, the sensor 130 connects to the patient cable 140 via a 15-pin sensor connector 110 designed to mate with a 15-socket patient cable connector 120. In various embodiments, the sensor connector 110 may have all of the pins electrically active, and, in other embodiments, only a subset of the pins may be active and used to communicate sensor signals. For example, in one embodiment only 9 pins are active. In other embodiments, the sensor connector may be a standard $SpO_2$ sensor, having, for example, a 9-pin mini-D connector, which is well known in the art. The latching member 800 disposed on the sensor connector 110 includes a latch protuberance 830 configured to engage a latch pocket 1310 disposed on the patient cable connector 120 so as to releasably hold the sensor connector 110 and patient cable connector 120 together. Advantageously, the sensor connector 110 and patient cable connector 120 are straightforwardly and efficiently connected by pressing them together until the latch protuberance 830 clicks into the latch pocket 1310. Advantageously, the sensor connector 110 and patient cable connector 120 are straightforwardly and efficiently separated by pulling them apart while pressing downward on the lever portion 810 of the latching member 800 with a thumb or finger, thereby disengaging the latch protuberance 830 from the latch pocket 1310. In one embodiment, the monitor connector 150 comprises a 20-pin DB connector. Physical aspects of the sensor side of the connector assembly are described generally with respect to FIGS. 6A-F and with greater detail with respect to FIGS. 7-11. Physical aspects of the patient cable side of the connector assembly are described generally with respect to FIGS. 12A-F and with greater detail with respect to FIGS. 13-16. One of ordinary skill in the art would recognize from the disclosure herein that a variety of pin numbers, mechanical mating shapes and the like are possible in various configurations.

FIGS. 6A-F illustrate one embodiment of a male sensor connector 110 having a front 601, back 602, top 603 and bottom 604. The back 602 terminates a sleeve 620 encasing a flex circuit 1000. In one embodiment, the sleeve is a two-part structure having a top 621 and a bottom 622 which interlock to create a channel which encloses the flex circuit 1000. In one embodiment, the sleeve is comprised of silicone. The flex circuit 1000 communicates signals between the sensor 130 and connector plug 900. A latching member 800 is disposed on the top 603 while being hingably mounted on each side thereof. The sensor connector 110 is configured to mate with a patient cable connector 120 by inserting the patient cable connector along alignment path 610. FIGS. 17A-F, described below, illustrate another embodiment of a male sensor connector.

FIGS. 7A-F illustrate one embodiment of a sensor connector shell 700 having a front 701, back 702, top 703, bottom 704, left side 705 and right side 706. The shell begins to taper from front 701 to back 702 at a point approximately midway between the front 701 and the back 702. The front 701 has a mating passageway 750 configured to accommodate a patient cable connector socket 1300. Proximate the front 701 is a mating ledge 730 configured to accommodate a recess 1222 located on the patient cable connector shell 1220. Housed within the sensor connector shell 700 is a positioning tab 780 which abuts the flex circuit pin plate 1040. Disposed on the upper right side 706 and left side 705 are aperture recesses 720 and apertures 721 configured to secure a latching member 800 by accommodating aperture pegs 860. The back 702 has a passageway 760 configured to accommodate the sleeve 620. Aperture peg 770 is proximate the back 702, extends vertically from bottom 704 to top 703, and is designed to engage the peg aperture 1050, securing the flex circuit 1000. In one embodiment, the sensor connector shell 700 is comprised of a PC-ABS blend. FIGS. 18A-F, described below, illustrate another embodiment of a male sensor connector shell.

FIGS. 8A-F illustrate one embodiment of a latching member 800 having a front 801, back 802, top 803 and bottom 804. The front 801 is generally rounded and has a latch portion 820 having a latch protuberance 830 located on bottom 804. In the illustrated embodiment, the latch protuberance 830 is a prism having right triangular bases and slopes downward from front 801 to back 802 of the latching member 800, so as to advantageously gradually engage and snap into the latch pocket 1310. The end of the latch protuberance 830 toward the back 802 of the latching member 800 is a flat surface configured to abut the flat edge of the latch pocket 1310 when snapped in. In various other embodiments, the latch protuberance 830 and latch pocket 1310 could be shaped differently. For example, in one embodiment, the latch protuberance 830 could be hemispherical in shape and the latch pocket 1310 shaped generally as a hemispherical depression to accommodate the latch protuberance 830. The back has lever portion 810 beginning at a point approximately ¾ of the way from front 801 to back 802, bending generally upward. Advantageously, the lever portion 810 and latching portion 820 are rigidly connected such that pressing downward with a finger or thumb on lever portion 810 raises the latching portion 820 and latch protuberance 830 so as to disengage the latch protuberance 830 from the latch pocket 1310. As such, the latching member 800 advantageously releasably holds the sensor connector 110 and patient cable connector 120 together, reducing accidental disconnects and providing for relatively straightforward and efficient connection and release. In certain embodiments, the latch protuberance 830 also disengages from the latch pocket 1310 and allows for disconnection without depressing the lever portion 810 of the latching member 800 when a certain threshold tension amount occurs on the connection between the latch protuberance 830 and the latch pocket 1310. This may be advantageous in certain cases, for example, if a sensor is accidentally jerked by a patient. In such a case, this tension release mechanism might reduce the chances of a monitor unit or other piece of equipment from being pulled onto the floor. In certain embodiments this tension release mechanism advantageously reduces the likelihood of potential accidents including damage to sensitive equipment and injuries to personnel. Attachment arms 840 are attached to either side of the latching member 800, are proximate the midway point from front 801 to back 802, and extend normally from the latching member 800. Attachment arms 840 further curve downward at the ends to accommodate a sensor connector shell 700 and terminate in aperture peg tabs 850. Aperture pegs 860 are attached to and extend inwardly from the aperture peg tabs 850 and accommodate the apertures 721 to secure the latching member 800 to the sensor connector shell 700. In one embodiment, the latching member 800 is comprised of a PC-ABS blend. FIGS. 19A-F, described below, illustrate another embodiment of a latching member.

FIGS. 9A-C illustrate one embodiment of a connector plug 900 having a front 901, back 902, top 903 and bottom 904. The connector plug 900 is disposed within and proximate the front 701 of the sensor connector shell 702. Socket pins 910 are arranged in rows and extend from front plate 920 through the pin apertures 950. The socket pins 910 are further designed to mate with the socket apertures 1331 disposed on the connector socket 1300. Additionally, the socket pins 910 are designed to extend through the pin apertures 1042 on the pin plate 1040 of the flex circuit 1000. The socket pins 910 include two detector pins 911 and thirteen drive pins 912, although many different configurations would be readily identifiable by a skilled artisan from the disclosure herein. Advantageously, shielding layers 940 wrap around back section 930 to provide enhanced signal noise protection. In one embodiment, the connector plug 900 is comprised of a PC-ABS blend, the shielding layers 940 are comprised of copper, and the socket pins 910 are comprised of a brass, bronze or copper base with gold plating. FIGS. 20A-C, described below, illustrate another embodiment of a sensor connector plug.

FIG. 10A-E illustrate one embodiment of the connector end of a flex circuit 1000 having a top 1001, bottom 1002, and front 1003. A rectangular pin plate 1040 is disposed at the front 1003 of the flex circuit 1000, having pin apertures 1042 arranged in rows and designed to accept socket pins 910. Flap 1041 is located on the detector pin side of pin plate 1040, on the face distal to connector plug 900. The flap 1041 is connected to the bottom of pin plate 1040 and folds over the pin plate 1040, leaving a small gap between the pin plate 1040 and the flap 1041. The flap is configured to contact at least the detector pins 911 and, advantageously, provides additional pin shielding and more robust connection between the flex circuit 1000 and the detector pins 911. A bend plate 1020 slopes downward from the top of the pin plate 1040 to the flex circuit length 1010. The circuit length 1010 extends to the sensor side of the flex circuit 1000 and communicates signals between the connector and sensor sides of the flex circuit 1000. In various embodiments, the flex circuit signals are shielded by ink layers or other shielding mechanisms. A peg aperture 1050 is on the circuit length, proximal the bend plate 1020 and is configured to accommodate the aperture peg 770, securing the flex circuit to the sleeve 620. In one embodiment, the flex circuit 1000 is comprised of alternating layers of Polyimide, rolled annealed copper, and silver impregnated thermoplastic ink which shields the signals. In various embodiments, the configuration of the layers and the materials used may differ. At least one memory unit 1030 is soldered to the bottom 1002 of flex circuit 1000 on bend plate 1020. In one embodiment, for example, the at least one memory unit 1030 is a 20K EEPROM well known to those of skill in the art and capable of performing various diagnostic and control functions. One of skill in the art will recognize from the disclosure herein that a variety of memory devices, controllers, microprocessors, gating or logic structures and the like may be used in various configurations. Advantageously, for example, the at least one memory unit 1030 is configured to assist in the determination of whether the sensor 130 is connected to compliant devices, such as patient cable connectors 120, patient cables 140 and monitors 160, thereby ensuring that the sensor 130 is also a compliant device. FIGS. 21A-E, described below, illustrate another embodiment of the connector end of a flex circuit.

Referring again to FIG. 9, in one embodiment, the drive pins 912 include eight emitter pins 913, two memory unit pins 914 connected to the memory unit 1030, a thermistor pin 915 connected to a thermistor and two shielding pins 916 connected to one or more of the various shielding components of the connector assembly. For example, the shielding pins 916 may connect to the shielding layers 940 or to the shielding shell 1500 discussed below with respect to FIG. 15.

The drive pins 912 of certain embodiments are separated from each adjacent drive pin by from about 0.09 inches to about 0.110 inches measured from the center of each pin. The detector pins 911 of certain embodiments are separated from the drive pins 912 by a greater distance than the drive pins 912 are separated from each other. For example, the detector pins 911 can be separated from adjacent drive pins 912 by from about 0.110 to about 0.130 inches measured from the center of each pin. The detector pins 911 can also be separated from each other by from about 0.110 to about 0.130 inches. For example, in one embodiment, the upper detector pin 911 is separated from the adjacent upper shielding pin 916 by about 0.130 inches and is separated from the lower detector pin by about 0.130 inches, while the lower detector pin 911 is separated from the adjacent lower shielding pin 916 by about 0.115 inches, while not necessary to all embodiments, having increased separation relative to the detector pins can advantageously help reduce noise in the relatively sensitive detector signals in certain embodiments.

As would be apparent to a skilled artisan from the disclosure herein, the drive pins 912 may be configured differently. For example, there may be a different number of emitter pins 913 (e.g., two), there may unused pins, or some of the drive pins 912 may be connected to other components in various configurations. In one alternative configuration, each detector pin 911 and/or drive pin 912 is separated from adjacent pins by from about 0.110 to about 0.115 inches.

FIGS. 11A-E illustrate one embodiment of the sensor end of flex circuit 1000 having a back 1101, top 1102, bottom 1103 and front 1104. The flex circuit terminates a first solder plate 1120 which is generally rectangular and connected to and is slightly wider than a first connection arm 1110. The first connection arm 1110 bends along its length in order to accommodate a second solder plate 1140. The second solder plate 1140 terminates a second connection arm 1130. In one embodiment, the first solder plate 1120 has three solder pads 1121 arranged in a triangular fashion and the second solder plate 1140 has ten smaller solder pads 1141 arranged in rows. It is well known in the art to include conductors and conductor paths on one or more sides of the flex circuit 1000. In various embodiments, the shape of the flex circuit 1000 may vary. For instance, in some embodiments, the flex circuit 1000 may vary in length, may not include a bend along the circuit length 1010, and the bend characteristics may vary.

FIGS. 12A-F illustrate one embodiment of a patient cable connector 120 having a front 1201, back 1202, top 1203 and bottom 1204. A connector socket 1300 protrudes from the front 1201 and is configured to accept connector plug 900 along alignment path 1210. The connector socket 1300 is described in greater detail with respect to FIGS. 13A-E. A connector shell 1220 has a semi-circular latching member recess 1221 configured to accommodate and secure the latching portion 820 of latching member 800. Additionally, the front 1201 face of shell 1220 has a recess 1222 which is configured to accommodate and secure the mating ledge 730 of the sensor connector shell 700. Raised grip striping 1223 is disposed on the top 1203 of the shell 1220 and reduce slipping of fingers when connecting and disconnecting the patient cable connector 120 and sensor connector 110. The shell 1220 terminates a cable opening 1224 which is configured to accept a strain relief 1600 and the patient cable 140. In some embodiments, a protruding feature is disposed on the back 1202 of connector shell 1220 over which a strain relief may be molded instead of being inserted into cable opening 1224. In various embodiments, the protruding feature may vary in flexibility. In one embodiment, the connector shell 1220 is comprised of a relatively hard polyvinyl choloride (PVC) material. In other embodiments, the connector shell may comprise a material similar to PVC or some other appropriate material.

FIGS. 13A-E illustrate one embodiment of a connector socket 1300 having a front 1301, back 1302, top 1303 and bottom 1304. The back portion 1340 of connector socket 1300 has a latch pocket plate 1320 having a latch pocket 1310. The latch pocket plate is disposed on top 1303 of the back portion 1340 of connector socket 1300. The latch pocket 1310 is generally a recessed pocket advantageously shaped and configured to releasably engage and retain latch protuberance 830 as described with respect to FIGS. 3-5 and FIGS. 8A-F above. In the illustrated embodiment, the latch pocket 1310 has a flat surface proximal the front 1301 of the socket 1300 so as to catch the flat edge of latch protuberance 830. The latch pocket 1310 is generally rectangular with rounded corners on the edge toward the back 1302 of the socket 1300 so as to accept the latch protuberance 830 snugly. As described above, the latch pocket 1310 may, in other embodiments, be shaped differently to accommodate various latch protuberance 830 shapes. For example, in certain embodiments, the latch pocket 1310 may be a hemispherical depression to accommodate a hemispherical latch protuberance 830. A bracing lip 1321 extends from latch pocket plate 1320 over the front portion 1330 of the connector socket 1300 and is configured to accommodate and secure the connector shell 1220 and the mating ledge 730 of sensor connector shell 700. The front portion 1330 has socket apertures 1331 arranged in rows configured to accept socket pins 910. Among the socket apertures 1331, in one embodiment, for example, are two detector socket apertures 1332 and thirteen drive socket apertures 1333 configured to accept detector pins 911 and drive pins 912 respectively. The socket apertures 1331 extend through the socket 1300 from front 1301 to back 1302. The detector socket apertures 1332 have a larger diameter in the back 1302 than the drive socket apertures 1333 to accommodate the detector socket shielding sleeves 1420. In one embodiment, the connector socket 1300 is comprised of a glass filled nylon or an equivalent material. In some embodiments, the glass filled nylon is appropriate because it is able to withstand repeated insertion and removal of the sensor connector 110.

Figure 14A:
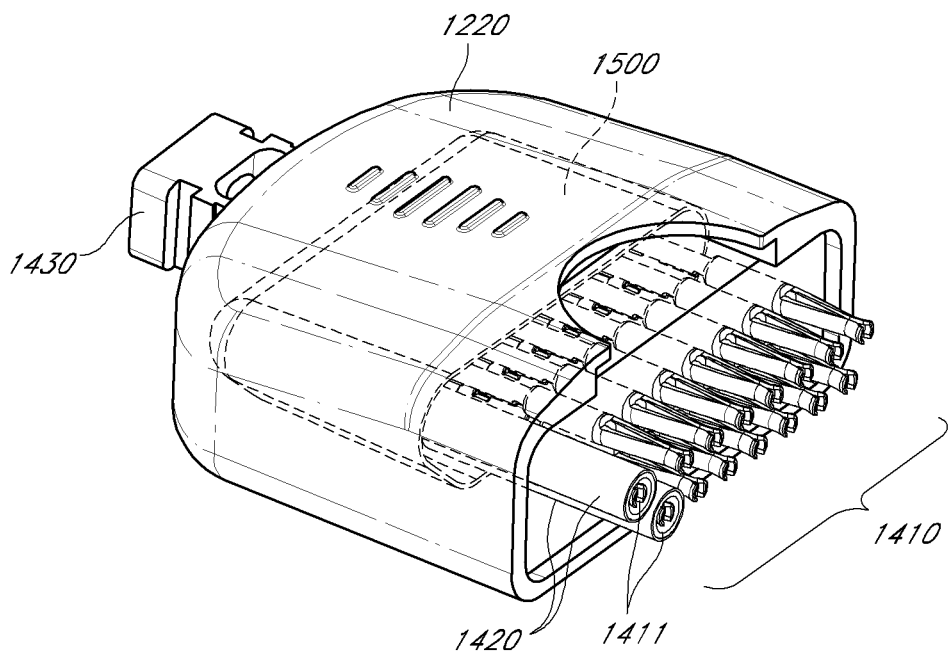
FIGS. 14A-B are front and back perspective exploded views, respectively, of a female patient cable connector, according to an embodiment of the disclosure.
Figure 14B:
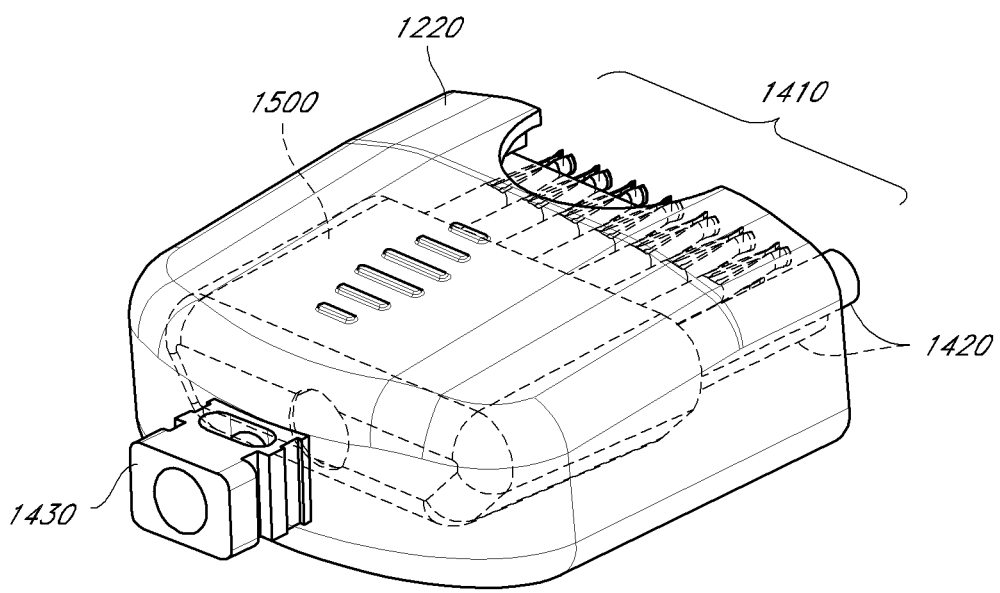

Emitter drive signals in a pulse oximetry system are relatively coarse and require relatively less noise protection to effectively drive the light emitters. In contrast, the detector signals must be transmitted from the sensor to the monitor with more precision and require relatively more noise protection to allow for accurate measurement of the sensor parameters. As such, enhanced shielding of the detector signals in the connection between the sensor and patient cable is desirable. FIGS. 14A-B illustrate one embodiment of socket shrouds 1410 encased by a shielding shell 1500 which is over-molded by the connector shell 1220. In this embodiment, the connector shell 1220 has a protruding member 1430 over which a strain relief may be overmolded. The socket shrouds 1410 are generally tubular and are configured accept and secure socket pins 910. The front portions of the socket shrouds 1410 extend through the socket apertures 1331. The back portions of the socket shrouds 1410 protrude from socket apertures 1331 are encased by the shielding shell 1500, which advantageously provides enhanced signal noise protection. Advantageously, the detector sockets 1411 are individually shielded by detector socket shielding sleeves 1420. This configuration provides for extra signal protection on the relatively sensitive detector signals. In various embodiments, the socket shrouds 1410 are comprised of various metals including brass, copper, bronze, copper or nickel. Moreover, in certain embodiments, the shrouds are plated in gold or another suitable material. In one embodiment, the shielding shell 1500 and detector socket shielding sleeves 1420 are made of copper and an inner plastic core. In some embodiments, the inner plastic core is comprised of Delrin or an equivalent material.

Figure 15A:
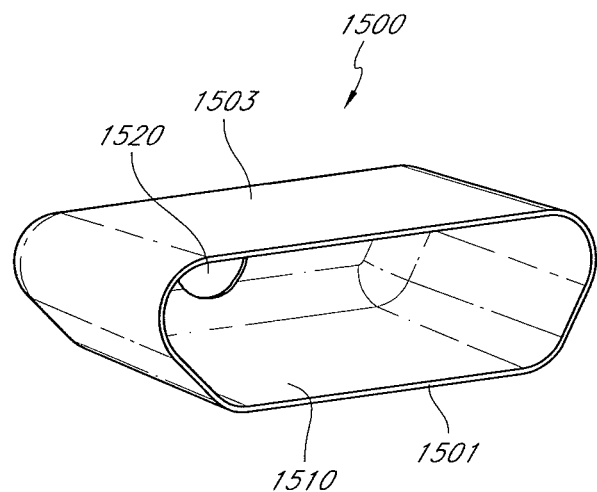
FIGS. 15A-C are front perspective, back perspective and side views of a shielding shell, respectively, according to an embodiment of the disclosure.
Figure 15B:
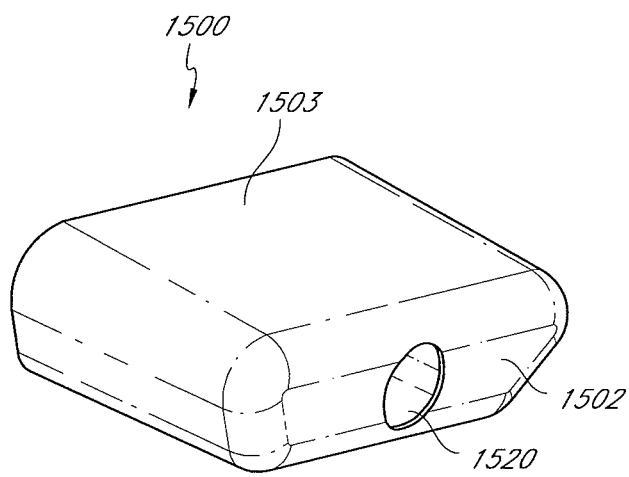
Figure 15C:
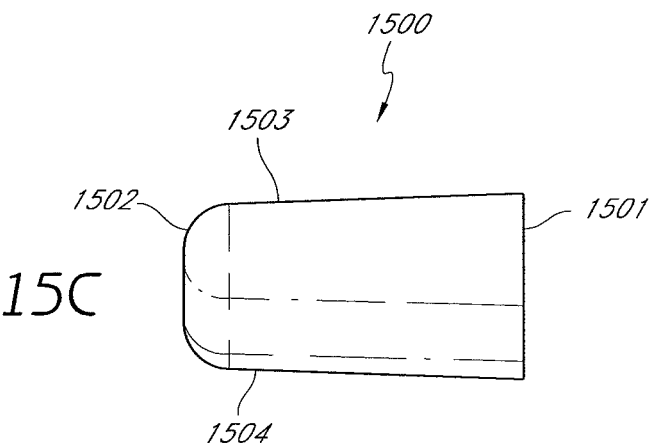
Figure 17A:
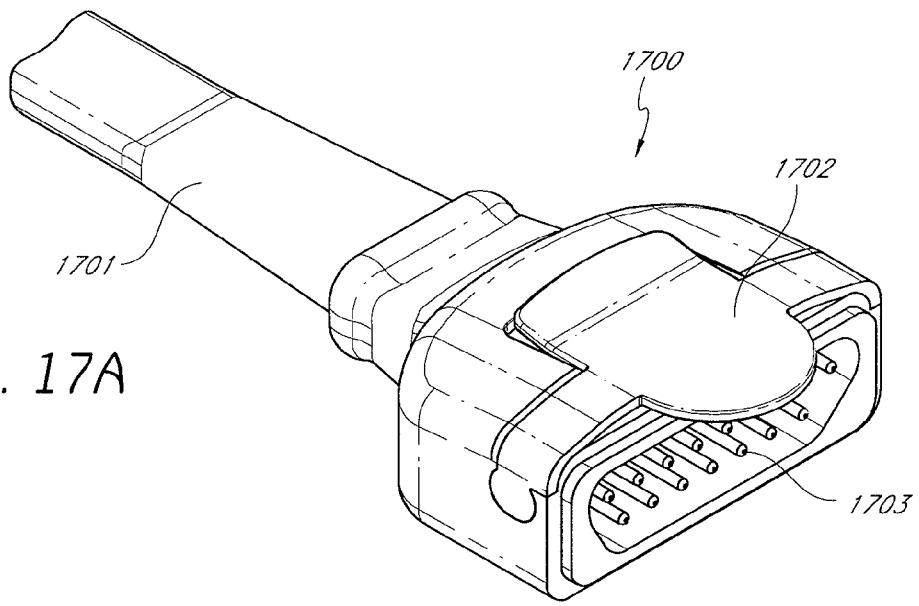
Figure 17B:
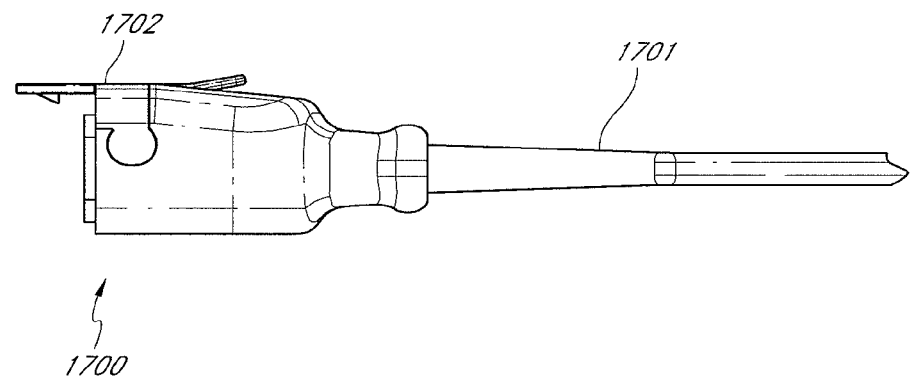
Figure 17E:
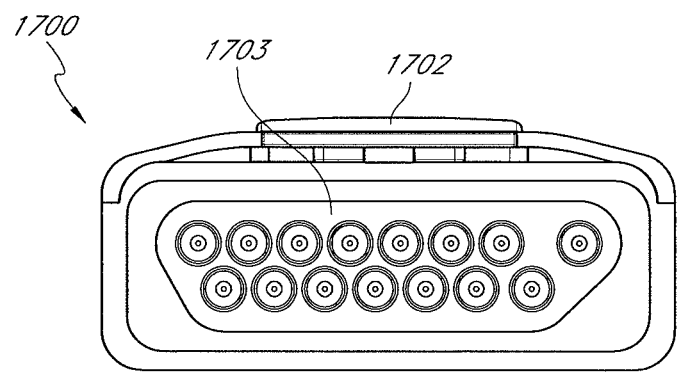
Figure 17F:
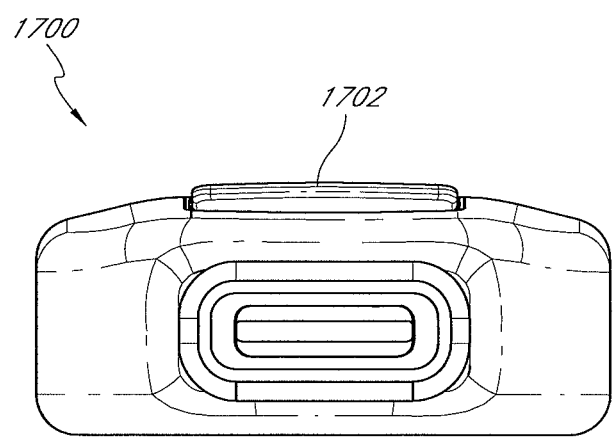
Figure 18A:
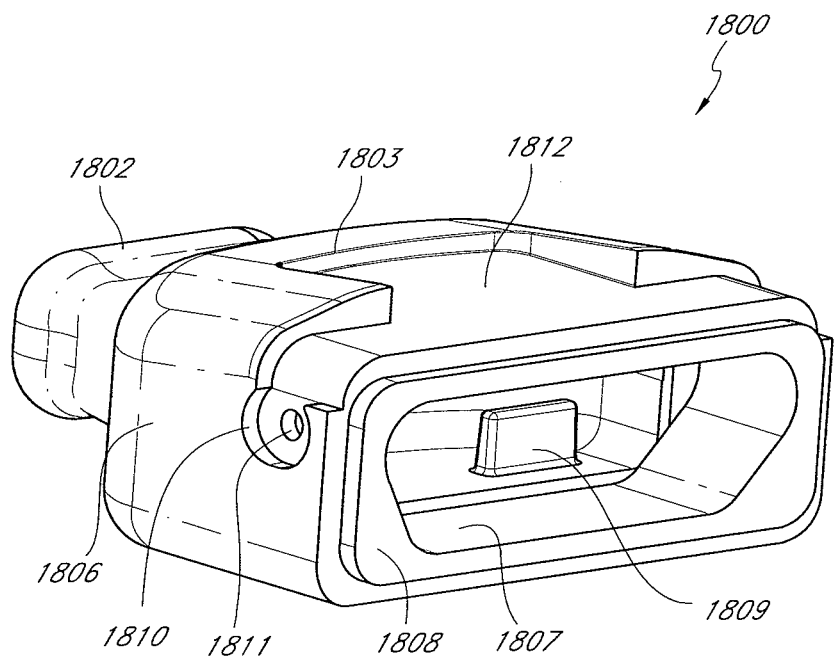
Figure 18B:
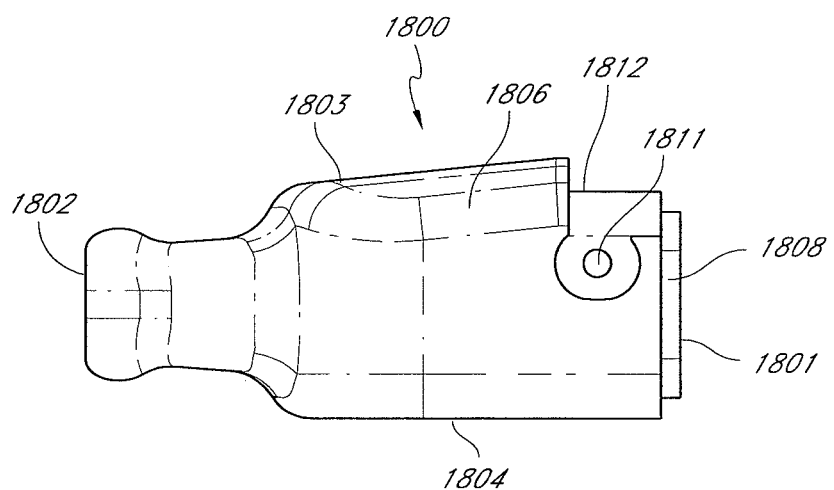
Figure 19A:
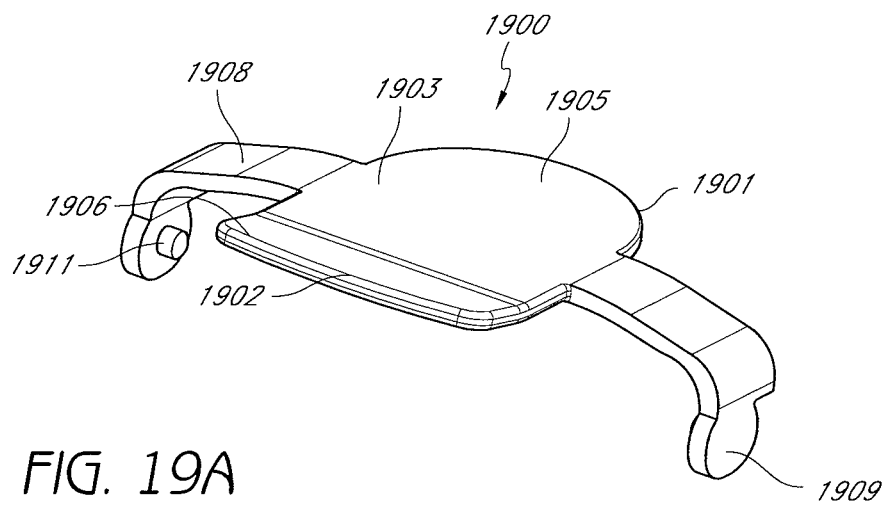
Figure 19B:
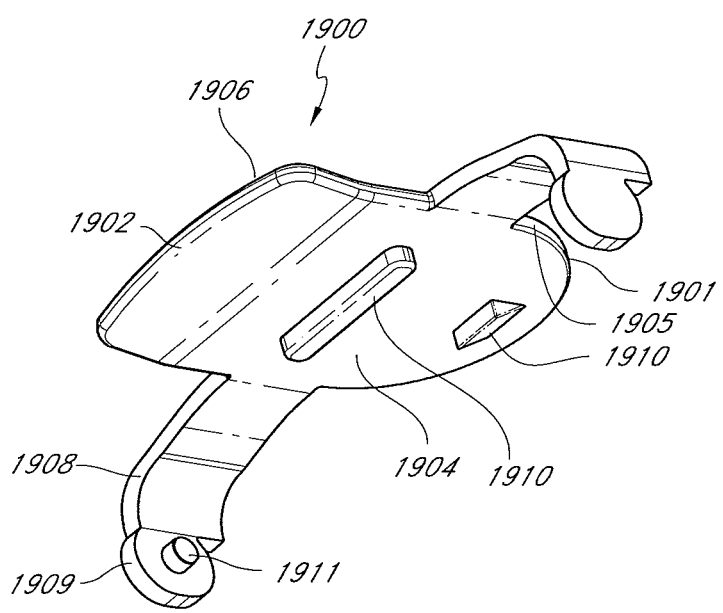
Figure 21A:
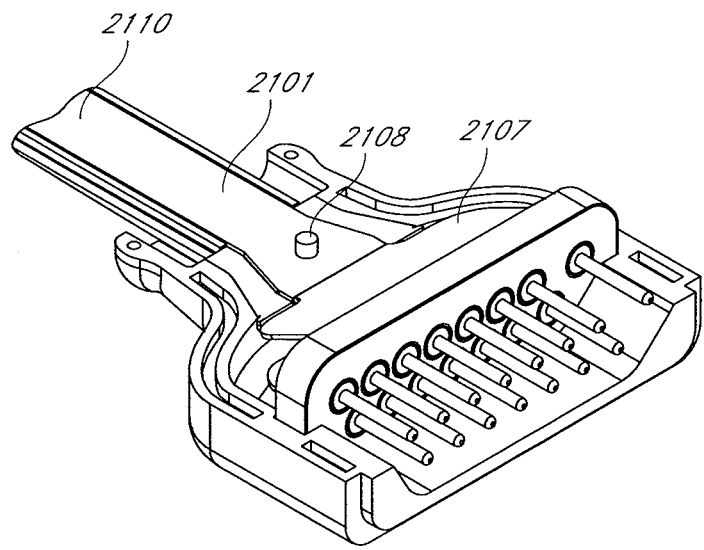
FIGS. 21A-E are perspective exploded, bottom perspective, side, top and bottom views, respectively, of the connector end of a flex circuit, according to another embodiment of the disclosure.
Figure 21B:
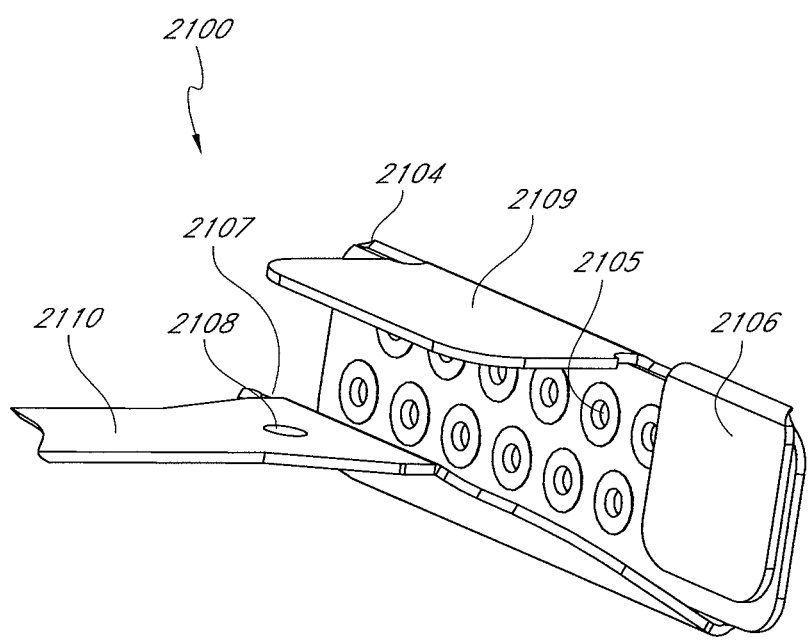
Figure 21C:
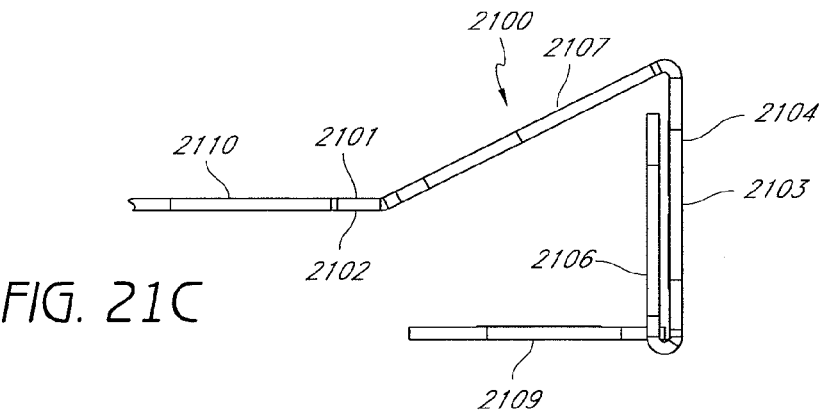
Figure 21D:
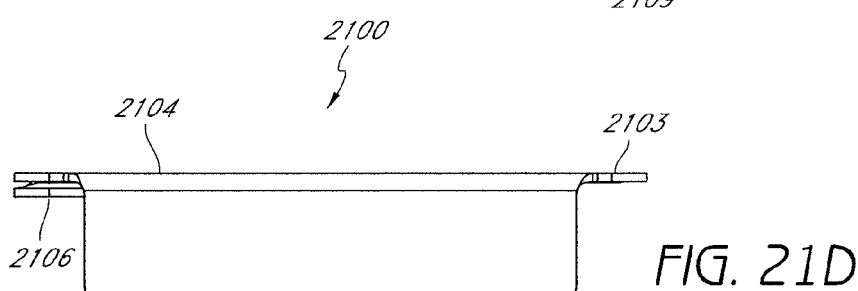
Figure 21E:
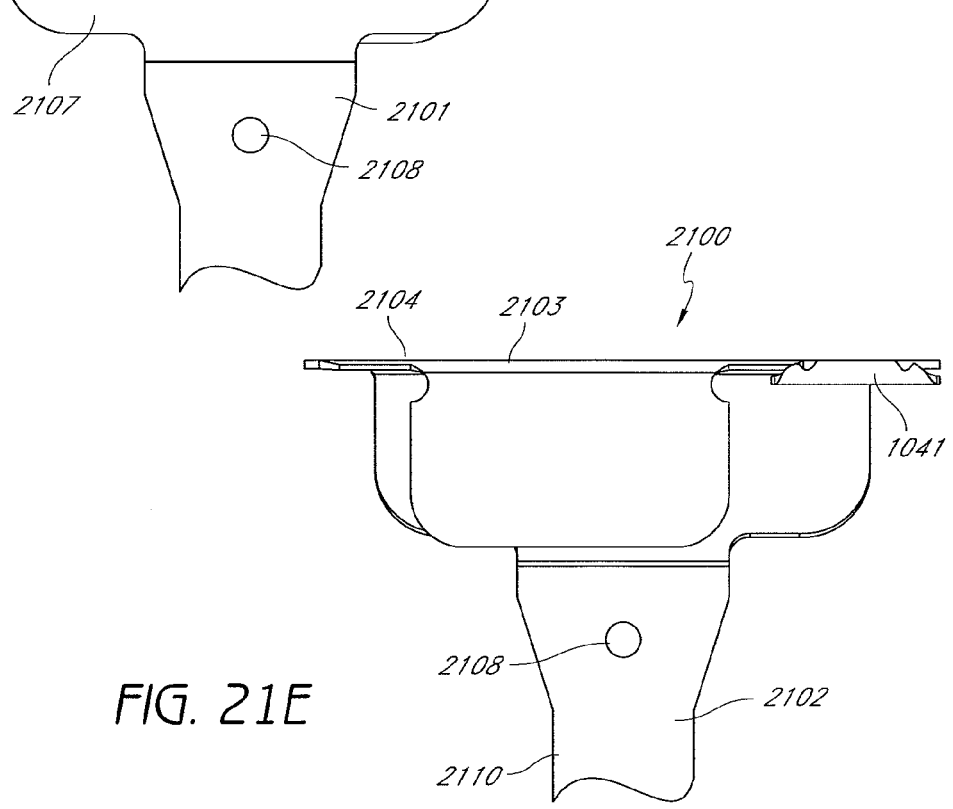
Figure 22A:
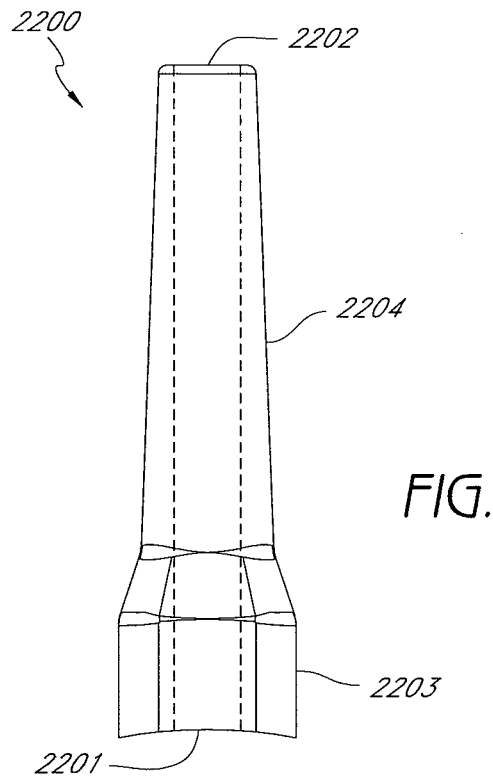
FIGS. 22A-D are top cross-sectional, side, front and back views of a strain relief, respectively, according to another embodiment of the disclosure.
Figure 22B:
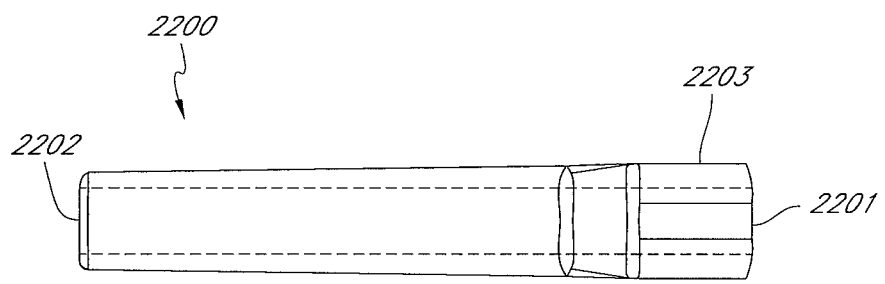
Figure 22C:
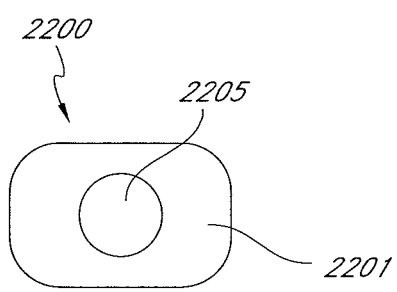
Figure 22D:
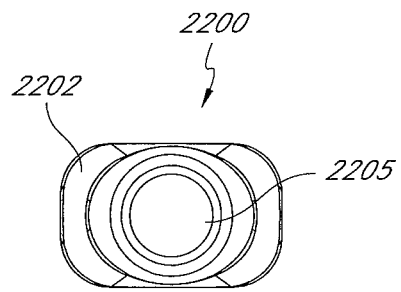

FIGS. 15A-C illustrate one embodiment of a shielding shell 1500 having a front 1501, back 1502, top 1503 and bottom 1504. The shielding shell 1500 is generally rectangular and hollow, having a socket housing opening 1510 at the front 1501. The back 1502 is generally closed except for a cable opening 1520 which is configured to accept the strain relief 1600 and the patient cable 140.

FIGS. 16A-E illustrate one embodiment of a strain relief 1600 that protects the patient cable 140 from bending forces and the cable wires and corresponding solder joints from pulling forces. The strain relief 1600 is a generally tapered cylinder having a front 1611, a back 1612, a head 1610, a tail 1620, and an axial cavity 1630 extending the length of the strain relief 1600. In one embodiment, the strain relief 1600 is over-molded on the patient cable 140 so that the patient cable 140 is retained within the axial cavity 1630 so formed. The head 1610 is disposed within the connector shell 1220, inserted through cable opening 1224, with the tail 1620 extending distal the shell 1220. The head 1610 consists of a cylinder which is narrower than the rest of the strain relief 1600 body and is configured to mate with the connector shell cable opening 1224 and the shielding shell cable opening 1520. The head 1610 terminates a securing plate which is encased within the shielding shell 1500 and secures the strain relief 1600 to the shielding shell 1500. In one embodiment, the strain relief 1600 is comprised of a low durometer PVC material. In other embodiments, the strain relief 1600 may comprise a material similar to PVC or some other appropriate material. In one embodiment, the strain relief 1600 and connector shell 1220 are over-molded at the same time so that the bend relief front 1611 fuses to the back of connector shell 1220. FIGS. 22A-D, described below, illustrate another embodiment of a strain relief.

FIGS. 17A-F illustrate another embodiment of a male sensor connector 1700. The sensor connector 1700 is generally similar in structure and function to the embodiment illustrated by FIGS. 6A-F, including a sleeve 1701 encasing a flex circuit, a latching member 1702, and a connector plug 1703.

FIGS. 18A-F illustrate another embodiment of a sensor connector shell 1800 having a front 1801, back 1802, top 1803, bottom 1804, left side 1805 and right side 1806. The shell 1800 is generally similar in structure and function to the embodiment illustrated by FIGS. 7A-F, including a mating passageway 1807, a mating ledge 1808, a positioning tab 1809, aperture recesses 1810, and apertures 1811, a back passageway 1813, and an aperture peg 1814. This embodiment also includes a latch member recess 1812 disposed on top 1803 and is configured to accommodate a latching member. The latch member recess 1812 generally extends across the entire top 1803 front 1801 portion of connector shell 1800 and extends towards the back 1802 in the middle portion of sensor connector shell 1800. In the illustrated embodiment, the latching member recess 1812 extends down the upper right side 1805 and left side 1806 and terminates at aperture recesses 1810. In the illustrated embodiment, aperture recesses 1810 are generally circular so as to strongly secure the latching member disposed on a patient cable connector. In this embodiment, the latch member recess 1812 is configured to allow the latching member to rock down into latch member recess 1812. As such, the latch member recess 1812 enhances the levering mechanism.

FIGS. 19A-F illustrate another embodiment of a latching member 1900 having a front 1901, back 1902, top 1903 and bottom 1904. The latching member 1900 is generally similar in structure and function to the embodiment illustrated by FIGS. 8A-F, including a latch portion 1905, a lever portion 1906, a latch protuberance 1907, attachment arms 1908, aperture peg tabs 1909, and aperture pegs 1911. This embodiment also includes a rib 1910 disposed on the bottom 1904 of latching member 1900 so as to provide a pivot surface with the connector shell. Moreover, in the illustrated embodiment, the aperture peg tabs 1909 are generally circular to fit the circular aperture recesses described with respect to FIGS. 18A-F above and strongly secure the latching member 1900 to the connector shell. In this embodiment, the rib 1910 and the aperture peg tabs 1909 are configured to allow for efficient pivoting of the latching member 1900, enhancing the levering mechanism.

FIGS. 20A-C illustrate another embodiment of a connector plug 2000 having a front 2001, back 2002, top 2003 and bottom 2004. The shell 2000 is generally similar in structure and function to the embodiment illustrated by FIGS. 9A-C, including socket pins 2005 comprising two detector pins 2006 and thirteen drive pins 2007, and pin apertures 2009. In the illustrated embodiment, the body of connector plug 2000 is comprised of a printed wiring board. Moreover, the front 2001 and back 2002 faces of the connector plug 2000 are covered with copper ground planes which act as a shielding mechanism. Also in the illustrated embodiment, a solder-mask is placed over both copper planes and a solder ring 2011 is placed around each pin aperture 2009 to connect the socket pins 2005. In the illustrated embodiment, the solder rings are isolated from the copper ground planes by a gap in the copper layer and one pin is electrically connected to the copper ground planes to complete the shield.

FIGS. 21A-E illustrate another embodiment of the connector end of a flex circuit 2100 having a top 2101, bottom 2102 and front 2103. The flex circuit 2100 is generally similar in structure and function to the embodiment illustrated by FIGS. 10A-E, and includes a pin plate 2104, pin apertures 2105, a first flap 2106, a bend plate 2107, and a peg aperture 2108. The illustrated embodiment also includes a second flap 2109 connected to the bottom of the pin plate 2104 and extending towards circuit length 2110. The second flap 2109 is configured to accommodate at least one memory unit which may, in some embodiments, be soldered to second flap 2109. The at least one memory unit is described above with respect to FIGS. 10A-E above.

FIGS. 22A-D illustrate another embodiment of a strain relief 2200. The strain relief 2200 is generally similar in structure and function to the embodiment illustrated by FIGS. 16A-D, having a front 2201, a back 2202, a head 2203, a tail 2204, and an axial cavity 2205. In the illustrated embodiment, the strain relief head 2203 is overmolded onto a protruding feature disposed on an embodiment of a patient cable connector shell instead of being inserted into the back of the connector shell. In one embodiment, the strain relief 1600 is comprised of a low durometer PVC material. In other embodiments, the strain relief 1600 may comprise a material similar to PVC or some other appropriate material.

Advantageously, various shielding mechanisms including, for example, in some embodiments, the shielding shell 1500, the detector socket shielding sleeves 1420, the shielding layers 940, and the flap 1041 are configured to reduce the unshielded area in an electrical connection between the sensor 130 and patient cable 140. In some embodiments, for example, the emitter and detector signals within the connector assembly 100 are shielded by various components as the signals are communicated from the sensor 130 to the patient cable 140 through the connector assembly 100. In some embodiments, for example, the various shielding components include the shielded flex circuit 1000, the flap 1041, shielding layers 940, the shielding shell 1500, and the shielded patient cable 140, thereby reducing the unshielded areas in the connection between the sensor and the monitor. Advantageously, in some embodiments, the detector signals are further shielded by detector socket shielding sleeves 1420, further reducing unshielded areas in detector signal path. For example, in certain embodiments, the detector signal path is substantially electrically shielded through substantially the entire connector assembly. In some embodiments, the emitter signals are also shielded by additional socket shielding sleeves 1420. In other embodiments, the flap 1041 covers the emitter pins 913 and/or other drive pins 912 as well as the detector pins 911.

Figure 23A:
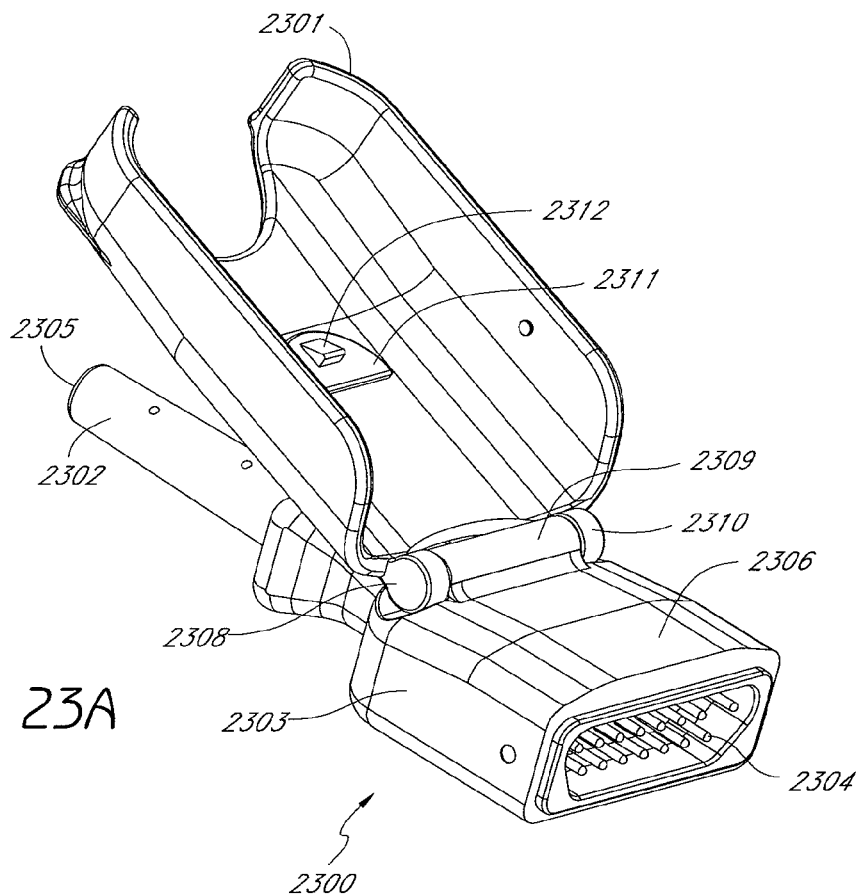
FIGS. 23A-B are front and bottom perspective views a male sensor connector, respectively, according to an embodiment of the disclosure.
Figure 23B:
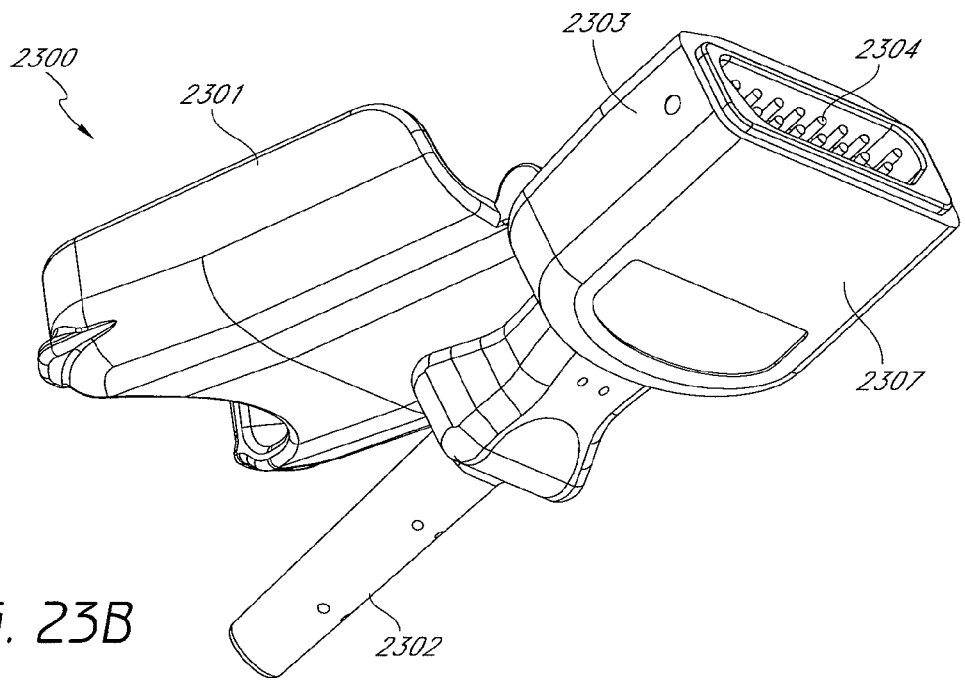
Figure 23C:
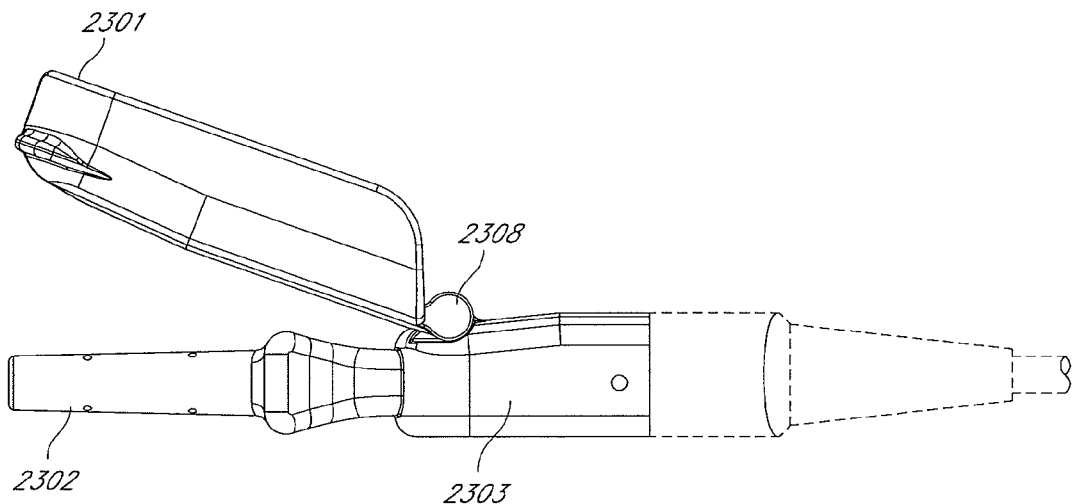
FIGS. 23C-D are side retainer hinged-open and side retainer hinged-closed views of a connector assembly, respectively, according to an embodiment of the disclosure.
Figure 23D:
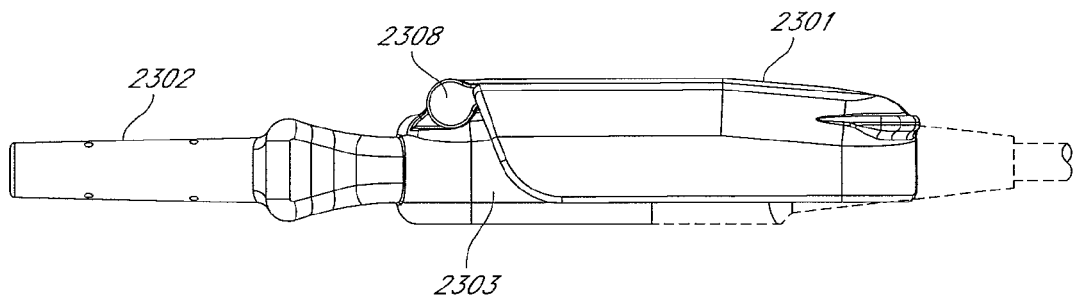

FIGS. 23A-B illustrate one embodiment of a male sensor connector 2300 having a front 2304, back 2305, top 2306 and bottom 2307. A retainer 2301 rotates about an axis 2308 and moves between an open position (FIGS. 23A-C) and a closed position (FIG. 23D). In the open position, the retainer 2301 allows for the sensor connector 2301 to be inserted into or removed from a patient cable connector such as one of the patient cable connectors described above. In the closed position, the retainer 240 mechanically impedes the sensor connector 220 from inadvertently disconnecting. Generally, the process of joining the connectors includes mechanically mating the connectors and hinging the retainer 2301 over mechanically mating structures of a patient cable to secure the connection and reduce accidental disconnects. The process of separating the connectors includes opening the retainer 2301 and pulling apart the sensor connector 2300 from the patient cable connector.

As a result of repeated wear and tear, or by other means, the retainer 2301 may become damaged. For example, if a certain threshold tension amount is placed on the connection between the sensor connector 2300 and the patient cable connector, the retainer 2301 may become damaged. The retainer 2301 may break off of the sensor connector shell 2303 if, for example, a sensor is accidentally jerked by a patient. In other cases, the connector may be dropped or smashed, damaging the retainer 2301.

If the retainer 2301 does become damaged, the portion of the system that the retainer 2301 is attached to can straightforwardly be replaced by hospital personnel or other users. In the illustrated embodiment, the retainer 2301 is advantageously disposed on the sensor connector 2300 rather than on a patient cable connector. In this configuration, in the event that the retainer 2301 becomes damaged, the sensor connector 2300 and attached sensor, and not the patient cable, may be replaced. The sensor may be a single use or disposable, both of which have shorter longevities than cable.

In certain embodiments, the retainer 2301 may allow the sensor connector 2300 to disengage from the patient cable connector without raising the retainer 2301 when a certain threshold tension amount is placed on the connection between the two sides of the connector assembly. For example, the retainer 2301 may be made of a material having a certain threshold flexibility such that the shape of the retainer gives way under a threshold tension, thereby releasing the opposing connector from the retainer 2300. This may be advantageous in certain cases, for example, if a sensor is accidentally jerked by a patient. In such a case, this tension release mechanism might reduce the chances of a monitor unit or other piece of equipment from being pulled onto the floor. In certain embodiments this tension release mechanism advantageously reduces the likelihood of potential accidents including damage to sensitive equipment and injuries to personnel.

In one embodiment, the back 2305 terminates a stress relief 2302. In an embodiment, the back 2305 terminates a flex-circuit instead of or in addition to the strain relief 2303. The sensor connector 2300 includes a shell 2303 and a retainer 2301, hingably attached to the top 2306, back of the shell 2303. In other embodiments, the retainer 2301 may be disposed on another portion of the shell 2303. For example, the retainer 2301 may be attached to a different side of the shell 2303, such as, for example, the bottom 2307. The retainer 2301 includes a latching member 2311 disposed on the underside of the retainer 2301. The latching member 2311 disposed on the retainer 2301 includes a latch protuberance 2312 configured to engage a latch pocket disposed on the patient cable connector so as to releasably hold the sensor connector 2300 and a patient cable connector together. The sensor connector 2300, for example, may be connected to the patient cable connector 120 described above and the latch protuberance may engage a latch pocket such as latch pocket 1310.

Figure 24A:
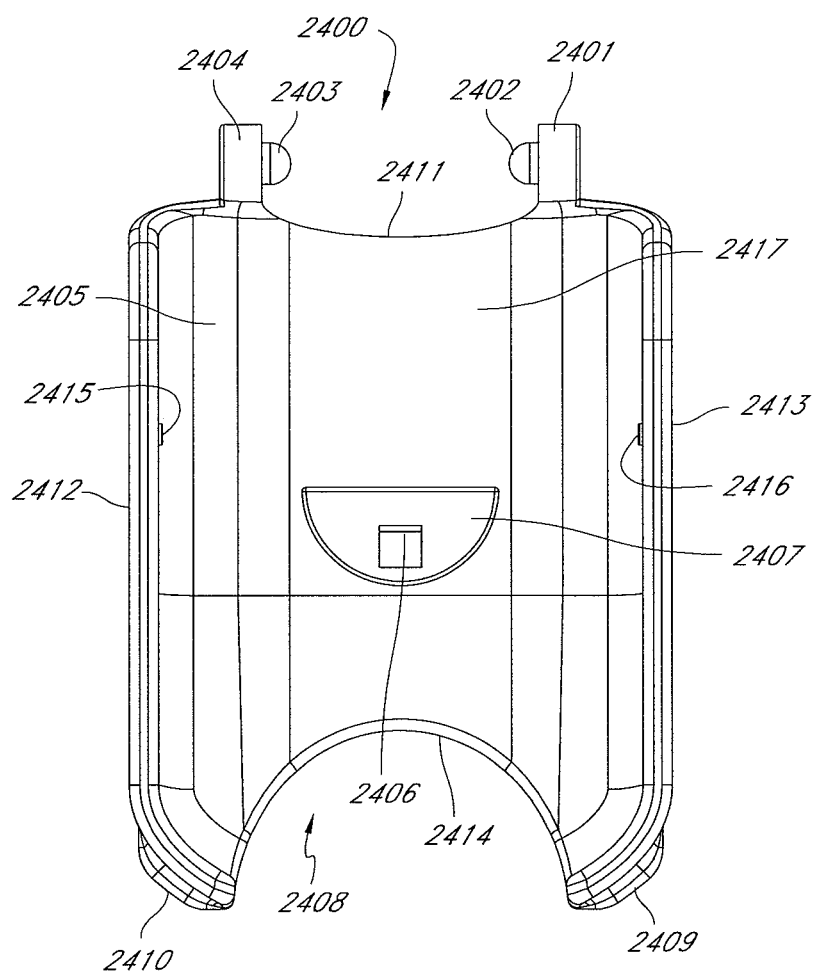
FIGS. 24A-C are bottom, perspective, and bottom perspective views of a sensor connector retainer according to an embodiment of the disclosure.
Figure 24B:
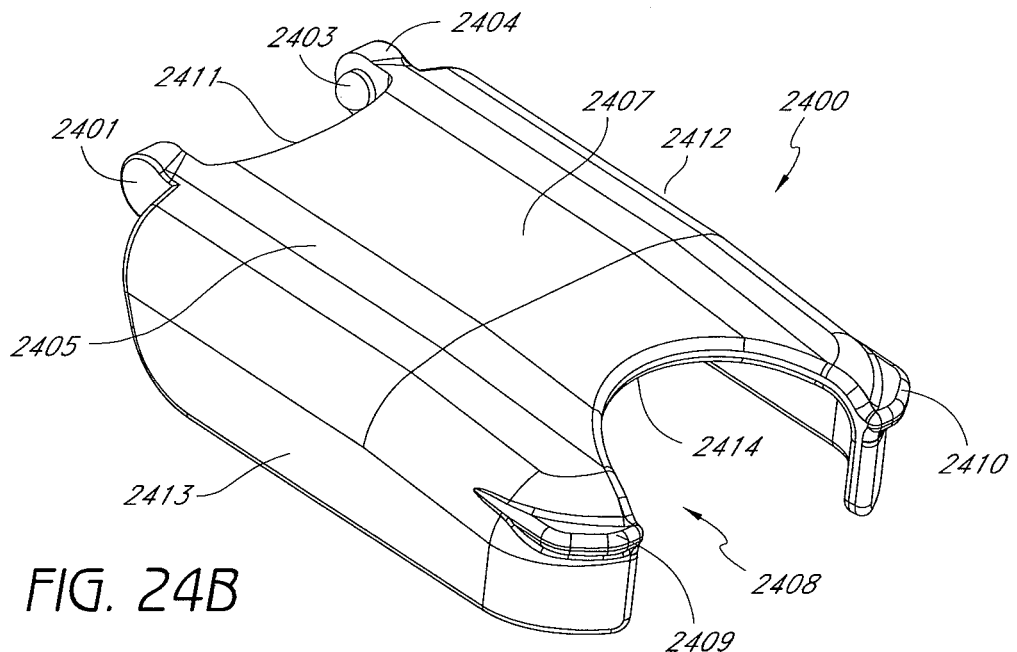
Figure 24C:
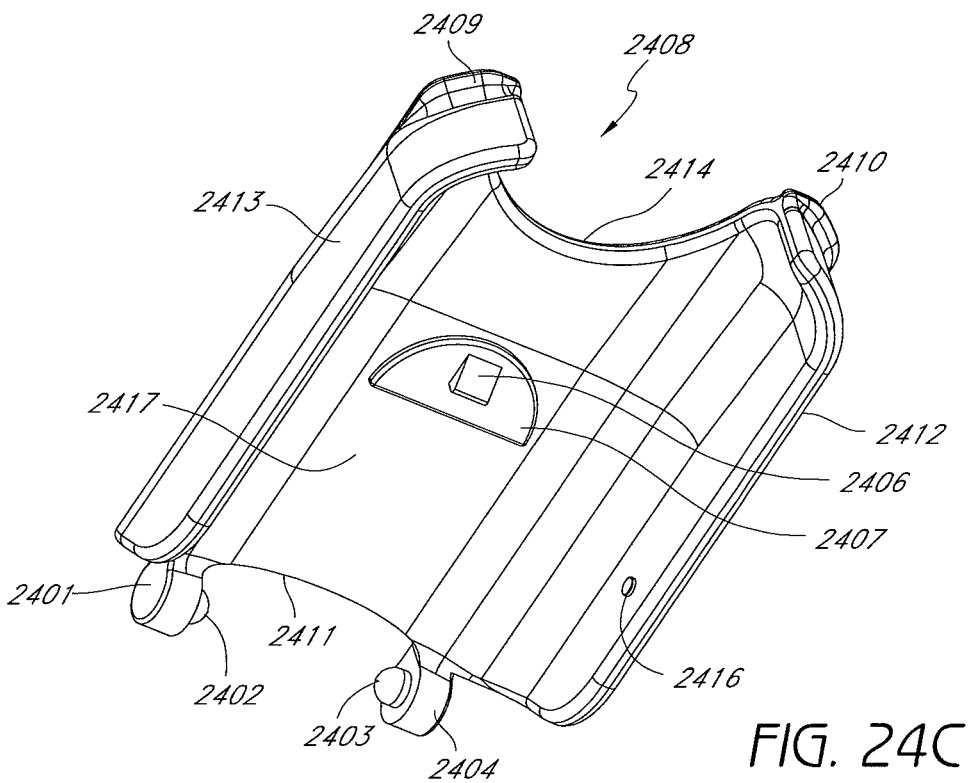
Figure 25A:
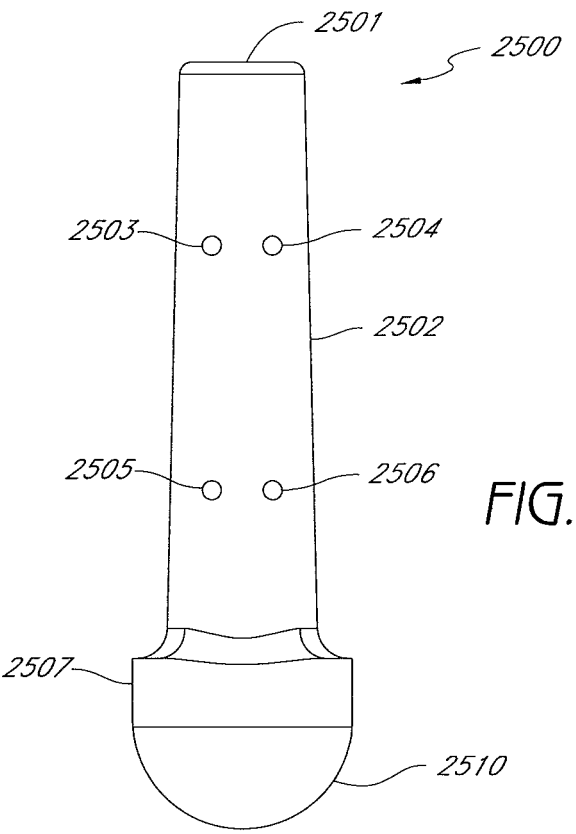
FIGS. 25A-D are top, side, front and back views of a strain relief, respectively, according to another embodiment of the disclosure.
Figure 25B:
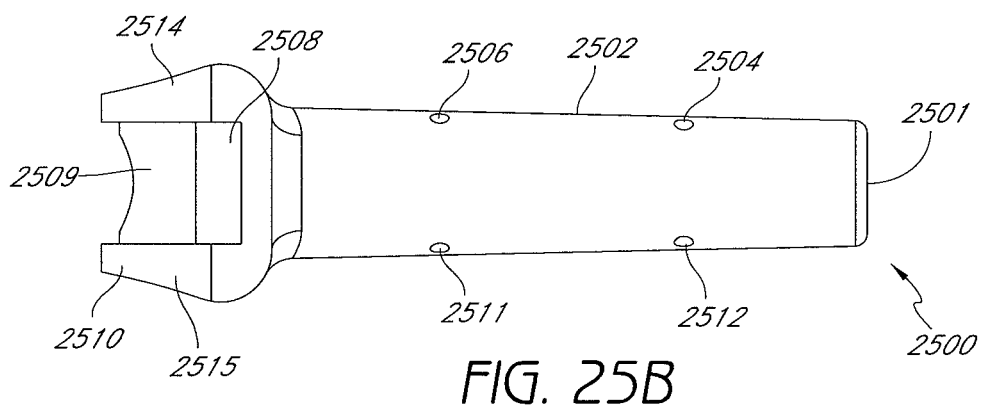
Figure 25C:
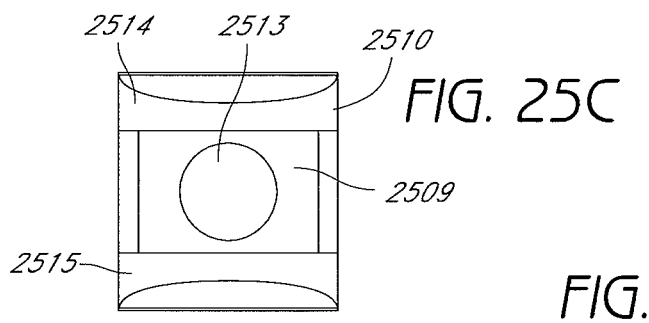
Figure 25D:
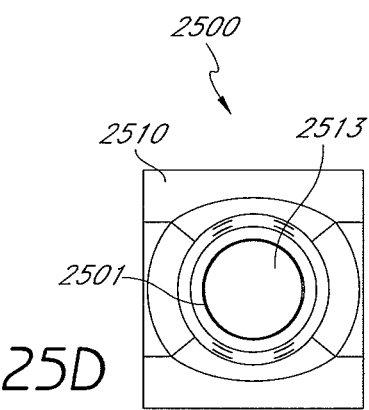

FIGS. 24A-B illustrate one embodiment of a retainer 2400 having a front 2414, back 2411, top 2407 and bottom 2417. The retainer 2300 is generally shaped as a molded shell which, when closed, may generally partially secure the mechanical mating of and/or electrical connection to another matable connector, thereby preventing disconnection. In one embodiment, the front 2417 of the retainer 2400 has a generally rounded cut-out section 2408. The cut-out section 2408 may be shaped to accommodate the other matable connector when the retainer 2400 is in a closed position. For example, the cut-out may be shaped so as to accommodate the patient cable and/or and the shape of the back portion of a matable patient cable connector. The back 2411 of the retainer 2400 has generally opposing tabs 2401, 2404, including pegs 2402, 2403 which allow the retainer 2400 to be mounted to a connector shell, such as, for example, connector shell 2303. The pegs 2402, 2403 mechanically mate in corresponding holes on a mounting portion of the connector shell. Once mated to the connector shell, the retainer 2400 is generally hinge rotatable about an axis generally coaxial with the pegs 2402, 2403. In other embodiments, the retainer 2400 may be connected to the connector shell in other manners as known in the art. For example, in another embodiment, the retainer 2400 may be connected to the retainer shell by a pin about which the retainer 2400 is rotatable. The retainer may be secured into place when in the closed position. For example, pegs 2405, 2406 snap into corresponding depressions in the connector shell, providing a snap-type fit. In other embodiments, the pegs may be located further towards the front 2408 of the shell and mate with corresponding depressions in the shell of the opposing connector shell, such as, for example, the shell of a patient cable connector. In other embodiments there may advantageously be more or less snapping features, other friction fit devices, or combinations or the like. For example, in one embodiment there are four pegs, two of which snap into corresponding features on the connector to which the retainer hingably attached and two of which snap into features on the opposing connector. In other embodiments, the securing mechanism may not be a peg and socket type snapping mechanism but may be some other mechanism, such as, for example, a friction type mechanism.

The retainer 2400 further includes a latching member 2407 located on the underside (bottom) 2417 of the retainer 2400 including a latch protuberance 2406. The front of the latching member 2407 comprises a rounded shape to generally accommodate a corresponding area including a latch pocket on a matable connector such as patient cable connector 120. In the illustrated embodiment, the latch protuberance 2406 comprises a prism having right triangular bases and slopes downward from back 2411 to front 2414, so as to advantageously engage and fit into the latch pocket on the opposing connector. The end of the latch protuberance 2406 toward the back 2411 of the latching member 2407 comprises a flat surface configured to abut the flat edge of the latch pocket of the opposing connector when snapped. In various other embodiments, the latch protuberance 2406 could be shaped differently. For example, in one embodiment, the latch protuberance 830 advantageously includes a hemispherical shape to accommodate, for example, a hemispherical latch pocket. In certain embodiments, the latch protuberance 2406 also disengages from the latch pocket 1310 and allows for disconnection without raising the retainer 2400 to an open position when a certain threshold tension amount is placed on the connection between the latch protuberance 2406 and the latch pocket of the matable connector. As discussed above, tension release mechanisms may be advantageous, for example, if a sensor is accidentally jerked by a patient. In such a case, this tension release mechanism reduces the chances of a monitor unit or other piece of equipment from being pulled onto the floor. In certain embodiments this tension release mechanism advantageously reduces a likelihood of potential accidents including damage to sensitive equipment and injuries to personnel. In one embodiment, the retainer 2400 is comprised of a PC-ABS blend.

The retainer 2400 comprises portions 2409, 2410 disposed on either side of the front 2414, top 2405 of the retainer 2400. The portions 2409, 2410 may be generally shaped so as to provide a surface to support the user's fingers lifting the retainer 2400. In other embodiments, there may be only one portion or more than two portions and the portions 2409, 2410 may be disposed on different parts of the retainer 2400. Moreover, the portions may comprise different shapes. For example, in some embodiments, the lifting portion or portions may provide a greater overall surface area to accommodate a large portion of the user's fingers.

FIGS. 25A-D illustrate an embodiment of a strain relief 2500. The strain relief 2500, may be, in some embodiments, generally similar in structure and function to the embodiment illustrated by FIGS. 16A-D and FIG. 22A-D, having a front 2510, a back 2510, a head 2507, a tail 2502. An axial cavity extends through the strain relief 2500 and is coaxial with the length of the tail 2502. In the illustrated embodiment, the strain relief head 2510 includes features 2509, 2510, 2514, 2515 adapted to accommodate corresponding features on a connector shell such as the connector shell 2303 described above. The strain relief 2500 may also be mated with features disposed on an embodiment of a patient cable connector shell instead of being inserted into the back of the connector shell. In one embodiment, the strain relief 2500 may be comprised of a low durometer PVC material. In other embodiments, the strain relief 2500 may comprise a material similar to PVC or some other appropriate material.

Figure 26A:
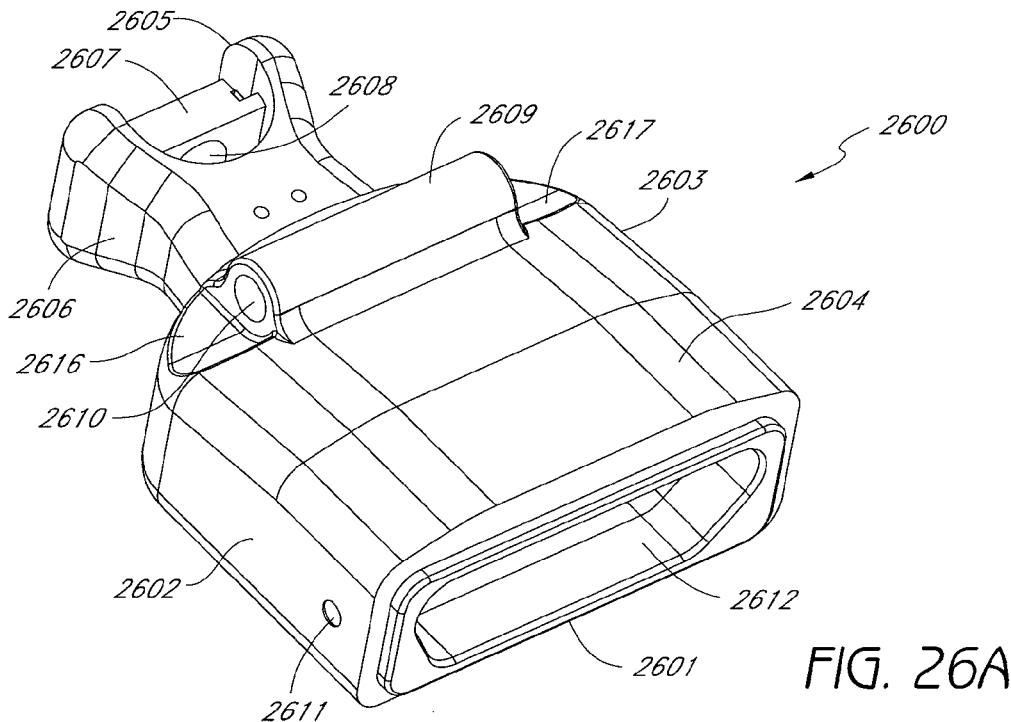
FIGS. 26A-B are perspective and bottom perspective views of a shell of a male sensor connector according to an embodiment of the disclosure.
Figure 26B:
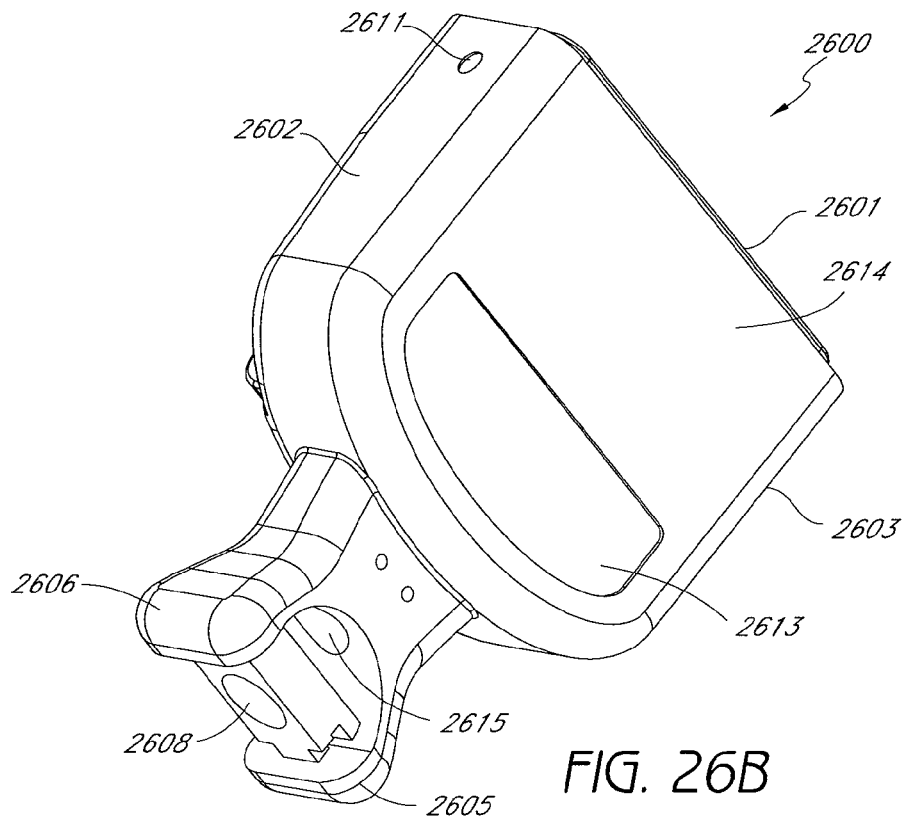

FIGS. 26A-B illustrate one embodiment of a connector shell 2600. The connector shell 2600 has a top 2604, bottom 2613, front 2601 and back 2605. The connector shell 2600 may be similar in certain aspects of its general structure and function to the connector shells described above such as connector shell 1800.

The connector shell terminates a tail section 2606 which is generally adapted to accommodate a sensor cable. For example, cavity 2608 may accept a sensor cable. In one embodiment, the shell comprises a shape generally adapted to accommodate a flex circuit such as the flex circuits described above or another flex circuit. The tail section 2606 also may include features such as features 2607 which accommodate a strain relief such as the strain reliefs 1600, 2200 described above. The connector shell 2600 includes a retainer mounting section 2609 with cavity 2610 which extends from one side of the shell 2600 to the other side. The cavity 2610 is adapted to accommodate, for example, pegs from a retainer such as the pegs 2402, 2403 of the retainer 2400 described above. In other embodiments, other attaching mechanisms may be used. For example, in another embodiment, the cavity 2610 and mounting section 2609 may accept a pin which extends through the entire mounting section and about which the retainer hinges. For example, in one embodiment, the cavity 2610 does not extend through the entire length of the mounting section 2609. Instead, there are depressions on either side of the mounting section 2609 deep enough to accept the corresponding pegs. The shell 2600 also includes depression 2611 and a similar depression on the other side of the shell 2600. As described above with respect to the retainer, the depression 2611 may secure a retainer such as retainer 2400 by mating with corresponding pegs on the hinged-closed retainer. As described above, other securing mechanisms may be used to secure the retainer.

A connector assembly has been disclosed in detail in connection with various embodiments. These embodiments are disclosed by way of examples only and are not to limit the scope of the claims that follow. One of ordinary skill in the art will appreciate the many variations and modifications.

For example, in various embodiments a sensor 130 may measure any type of physiological parameter. In other embodiments, the monitor 160 end of the patient cable 140 might be configured to communicate with any type of monitor 160.

In addition, the pins and/or sockets of the sensor connector 110 and/or patient cable connector 120 of the connector assembly may be configured differently, allowing for compatibility with multiple types of sensors 130 and patient cables 140 and corresponding types of monitors. For example, the patient cable 140 along with embodiments of the patient cable connector 120 may be designed to work with sensors 130 having different numbers of active pins. In such embodiments, the signal conduits on the patient cable connector 120 (e.g., the conduits going through the socket shrouds) corresponding to active signals of the corresponding sensor are electrically connected, while the remaining conduits remain electrically inactive. In such embodiments, the patient cable connector 120 can be used with sensors 130 having less active pins, for example. In one example, the patient cable 140 and patient cable connector 120 can be designed to interact with an SpO$_2$ sensor having nine active drive pins and 2 active detector pins. In another example, such as for the embodiments described above (e.g., with respect to FIG. 9), the patient cable 140 and patient cable connector 120 are configured to operate with a sensor 130 having 13 active drive pins (e.g., an enhanced oximetry sensor for the measurement of multiple patient parameters).

In some embodiments, a sensor 130 and sensor connector 110 may be configured to operate with multiple types of patient cables 140 and/or patient cable connectors 120. For example, an enhanced oximetry sensor 130 and associated sensor connector 110 may be compatible with a patient cable 140 and patient cable connector 120 configured to operate with an enhanced oximetry sensor 130 (such as those described above with respect to FIGS. 12-16) and with a patient cable 140 and patient cable connector 120 configured to operate with a sensor having less active pins, such as an SpO$_2$ sensor 130, for example. In such an embodiment, an enhanced oximetry sensor 130 and sensor connector 110, when connected with a patient cable 140 and patient cable connector 120 configured to operate with an enhanced oximetry sensor, may be capable of providing the functionality of the enhanced sensor. On the other hand, the enhanced sensor 110 may also be configured to perform the functions of an SpO$_2$ sensor when connected with a patient cable 140 and patient cable connector 120 configured to operate with an SpO$_2$ sensor. In one example configuration, the sensor 110 is an SpO$_2$ sensor and the sensor connector 130 has nine active drive pins, four of which are electrically connected on the connector to form two sets of two emitter pins. In such a configuration, a patient cable 140 and corresponding patient cable connector 120 configured to operate with an enhanced oximetry sensor are compatible with the SpO$_2$ sensor and sensor connector to provide SpO$_2$ functionality to the monitor.

The compatibility of the connector assembly with different types of patient cables 140 and sensors 130 can advantageously provide general compatibility between components of different systems (e.g., between enhanced oximetry systems and SpO$_2$ systems). One of skill in the art will recognize from the disclosure provided herein that other configurations are possible and that the connector assembly may provide compatibility between other types of systems.

In alternative configurations, different types of electrical components can be used. For example, the flex circuit 1000 may be replaced by a set of insulated, bundled leads. In embodiments where a cable is used, the flex circuit shell (e.g., the flex circuit shell 1701) and/or connector shell (e.g., the connector shell 1800) may be replaced by, for example, an overmolded part encasing at least a part of the cable and components of the sensor connector (e.g., the connector plug 2000 and/or associated printed wiring board). In some scenarios, sensors designed for single patient use comprise a cable and sensors designed to be reusable comprise a flex circuit.

In some embodiments, the number of socket pins 910 and corresponding socket apertures 1331 may vary. Additionally, in some embodiments, the construction materials for various components may generally vary. For example, in some embodiments, some of the components can be made of different types of metal including, but not limited to, copper, tungsten, nickel, and others. In other embodiments, some of the components can be made of different types of plastic. In yet other embodiments, some components described may be substituted for other implementations that provide the desired function. For example, in some embodiments, the flex circuit 1000 may not be used and may be substituted for by, for example, a cable, another type of circuit or other signal communication mechanism. In other embodiments, for example, the sensor connector shell 700 and the patient cable connector shell 1220 may be replaced by an overmold. In some embodiments, the overmold is comprised of a PVC material. In other embodiments, the overmold and/or other components of the connector assembly may comprise PVC, a material similar to PVC or some other appropriate material.

Further, the memory unit 1030 may vary in memory storage size in various embodiments. In various embodiments, the memory unit 1030 may be a flash device, an EEPROM, an EPROM, a memory circuit, or another type of memory device. Moreover, the memory unit 1030 may be capable of various functions. For example, in various embodiments, the memory unit 1030 may store a sensor type, a patient type, parameter calculation data, or other information generally useful to a micro-processor. For example, in some embodiments, the memory unit 1030 may be able to store information on upgrades to parameter calculation algorithms or initialization data. In still other embodiments, the memory unit 1030 may include control logic or be combined with a microprocessor to provide added functionality. In addition, in certain embodiments, the memory unit 1030 may be located at various locations including, for example, the patient cable connector 120, the patient cable 140, the sensor 130, or along the flex circuit 1000.

In still other embodiments, the latching mechanism may be implemented in different ways. For example, in some embodiments the latching mechanism may include a squeeze mechanism disposed on the side of the connector assembly 100. In other embodiments, the latching mechanism may be disposed on the bottom of the connector assembly 100. In yet other embodiments, there may be latching mechanisms disposed on both the top and bottom of the connector assembly 100. In other embodiments, the latching mechanism may be implemented by a friction mechanism rather than, or in addition to, a latch and pocket mechanism. For example, in some embodiments, a friction hood extending from one side of the connector assembly 100 over a portion of the other side may be used to secure a connection using friction instead of a latch and pocket mechanism.

In various embodiments, the various mechanical parts of the connector assembly 100 may be generally reversed. For example, in some embodiments, the sensor connector 110 may be a female connector and the patient cable connector 120 may be a male connector. Moreover, in some embodiments, the latching mechanism may be reversed. For example, in some embodiments the latching member 800 may be disposed on the patient cable connector 120 and the latch pocket 1310 may be disposed on the sensor connector 110.

What is claimed is:

1. An apparatus in a noninvasive patient monitoring system, the apparatus configured to generate detector signals indicative of attenuation of light by body tissue and to communicate the signals via a shielded connection, the apparatus comprising:

a patient sensor and a patient cable, the patient sensor comprising sensing componentry configured to emit light and generate detector signals indicative of attenuation of light by body tissue;

first and second connectors releasably attached to one another, the first connector mechanically irremovably coupled to one of the patient sensor and the patient cable and the second connector mechanically irremovably coupled to the other of the patient sensor and the patient cable, wherein, when in the relesably attached configuration, a physiological patient monitor communicates emitter signals through the first and second connectors to the sensing componentry, and wherein the detector signals are communicated through the first and second connectors to the monitor;

a plurality of emitter conductor segments each configured to communicate an emitter signal and one or more detector conductor segments each configured to communicate a detector signal, each emitter conductor segment and each detector conductor segment comprising a first portion supported by the first connector and a second portion separably mating with the with the first portion and supported by the second connector; and one or more elongate detector shields supported by one or more of the first connector and the second connector, each detector shield surrounding and extending along the length of at least a portion of one or more of the detector conductor segments, the emitter conductor segments disposed outside the one or more detector shields.

2. The apparatus of claim 1, wherein the first portion of each detector conductor segment comprises an elongate pin, wherein the second portion of each detector conductor segment comprises an elongate shroud releasably receiving a corresponding one of the pins, and wherein each detector shield surrounds and extends along the length of at least a portion of one of the elongate shrouds and its corresponding elongate pin.

3. The apparatus of claim 2, further comprising a first metallic shield layer, supported by one of the first connector and the second connector, and wrapped around at least a portion of each emitter conductor segment and at least a portion of each detector conductor segment.

4. The apparatus of claim 3, further comprising a second metallic shield layer supported by the other of the first connector and the second connector, and wrapped around at least a portion of each emitter conductor segment and at least a portion of each detector conductor segment.

5. The apparatus of claim 4, wherein, in the releasably attached configuration, substantially the entire length of each of the first and second portion of each detector conductor segment is disposed within one or more of the corresponding detector shield, the first metallic shield layer, and the second metallic shield layer.

6. The apparatus of claim 1, wherein each of the one or more detector shields surrounds and extends along the length of a portion of a single corresponding detector conductor segment.

7. The apparatus of claim 1, wherein each of the one or more detector shields comprises a cylindrical sleeve.

8. The apparatus of claim 1, wherein the one or more detector shields comprise metal.

9. The apparatus of claim 1, further comprising:
a first latching element attached to the first connector and a corresponding second latching element attached to the second connector,
the first and second latching elements configured to engage with one another to provide the releasable attachment between the first connector and the second connector.

10. The apparatus of claim 9, wherein the first latching element pivots to disengage from the second latching element when the first latching element is mechanically actuated by a user.

11. The apparatus of claim 10, wherein the first latching element is configured to pivot when subject to a threshold amount of tension.

12. The apparatus of claim 10, wherein the first latching element pivots in response to thumb actuation by a user.

13. The apparatus of claim 9, wherein one of the first and second latching elements comprises a pocket, and the other of the first and second latching elements comprises a protuberance configured to engage with the pocket.

14. A method of operating an apparatus in a noninvasive patient monitoring system, the apparatus configured to generate detector signals indicative of attenuation of light by body tissue and configured to communicate the detector signals via a shielded connection, the method comprising:
providing an apparatus comprising:
a patient sensor and a patient cable, the patient sensor comprising sensing componentry configured to emit light and generate detector signals indicative of attenuation of light by body tissue;
first and second connectors releasably attached to one another, the first connector mechanically irremovably coupled to one of the patient sensor and the patient cable and the second connector mechanically irremovably coupled to the other of the patient sensor and the patient cable, wherein, when in the releasably attached configuration, a physiological patient monitor communicates emitter signals through the first and second connectors to the sensing componentry, and wherein signals generated by the optical detectors are communicated through the first and second connectors to the monitor;
a plurality of emitter conductor segments each configured to communicate an emitter signal and one or more detector conductor segments each configured to communicate a detector signal, each emitter conductor segment and each detector conductor segment comprising a first portion supported by the first connector and a second portion separably mating with the with the first portion and supported by the second connector; and
one or more elongate detector shields supported by one or more of the first connector and the second connector, each detector shield surrounding and extending along the length of at least a portion of one or more of the detector conductor segments, the emitter signal conductors disposed outside the one or more detector shields;
mechanically actuating a first latching element attached to the first connector to disengage the first latching element from a second latching element attached to the second connector; and
detaching the first connector from the second connector.

15. The method of claim 14, wherein said mechanically actuating causes the first latching element to pivot to disengage from the second latching element.

16. The method of claim 15, wherein the first latching element is configured to pivot when subject to a threshold amount of tension.

17. The method of claim 15, wherein the first latching element pivots in response to thumb actuation by a user.

18. The method of claim 14, wherein one of the first and second latching elements comprises a pocket, and the other of the first and second latching elements comprises a protuberance configured to engage with the pocket.

19. The method of claim 14, wherein the first portion of each detector conductor segment comprises an elongate pin, wherein the second portion of each detector conductor segment comprises an elongate shroud releasably receiving a corresponding one of the pins, and wherein each detector shield surrounds and extends along the length of at least a portion of one of the elongate shrouds and its corresponding elongate pin.

20. The method of claim 19, further comprising:
a first metallic shield layer, supported by one of the first connector and the second connector, and wrapped around at least a portion of each emitter conductor segment and at least a portion of each detector conductor segment; and
a second metallic shield layer supported by the other of the first connector and the second connector, and wrapped around at least a portion of each emitter conductor segment and at least a portion of each detector conductor segment.

* * * * *

UNITED STATES PATENT AND TRADEMARK OFFICE
CERTIFICATE OF CORRECTION

PATENT NO. : 8,529,301 B2  
APPLICATION NO. : 13/399762  
DATED : September 10, 2013  
INVENTOR(S) : Al-Ali et al.

Page 1 of 1

It is certified that error appears in the above-identified patent and that said Letters Patent is hereby corrected as shown below:

In the Specification

Column 8 at line 20, Change "choloride" to --chloride--.

In the Claims

Column 17 at line 14, In Claim 1, Change "with the with the" to --with the--.

Column 18 at lines 36-37, In Claim 14, Change "with the with the" to --with the--.

Signed and Sealed this  
Fifteenth Day of April, 2014

Michelle K. Lee  
*Deputy Director of the United States Patent and Trademark Office*